United States Patent [19]

Cron et al.

[11] 4,347,354

[45] Aug. 31, 1982

[54] PREPARATION OF 1-N-[ω-AMINO-α-HYDROXYALKANOYL-]AMINOGLYCOSIDE POLYSILYLATED ANTIBIOTICS AND PRODUCTS OBTAINED THEREFROM

[75] Inventors: Martin J. Cron, Fayetteville; John G. Keil, Manlius; Jeng S. Lin, Clay; Mariano Ruggeri, Liverpool; Derek Walker, Jamesville, all of N.Y.

[73] Assignee: Bristol-Myers Company, New York, N.Y.

[21] Appl. No.: 192,656

[22] Filed: Oct. 1, 1980

Related U.S. Application Data

[63] Continuation of Ser. No. 33,912, Apr. 27, 1979, abandoned, which is a continuation-in-part of Ser. No. 896,430, Apr. 14, 1978, abandoned, which is a continuation-in-part of Ser. No. 791,806, Apr. 28, 1977, abandoned.

[51] Int. Cl.$^3$ .................................. C07H 15/22
[52] U.S. Cl. .................................. 536/10; 424/180; 536/12; 536/17 R
[58] Field of Search .................. 536/17 R, 10, 12

[56] References Cited

U.S. PATENT DOCUMENTS

| | | | |
|---|---|---|---|
| 4,029,882 | 6/1977 | Wright | 536/17 |
| 4,029,883 | 6/1977 | Hiraga et al. | 536/17 |
| 4,055,715 | 10/1977 | Tomioka et al. | 536/17 |

OTHER PUBLICATIONS

Tsuchiya et al., "Tetrahedron Letters", No. 51, pp. 4951-4954.

Cron et al., "ACS Symposium Series #125 Amino Cyclitol Antibiotics", Amer. Chem. Soc., Washington, D.C., 1980, pp. 247-254.

*Primary Examiner*—Johnnie R. Brown
*Attorney, Agent, or Firm*—Richard R. Lloyd

[57] ABSTRACT

An improved process for the preparation of 1-N-[ω-amino-α-hydroxyalkanoyl]aminoglycoside antibiotics comprises acylating a polysilylated aminoglycoside antibiotic in a substantially anhydrous organic solvent with an acylating derivative of an ω-amino-α-hydroxyalkanoic acid.

30 Claims, No Drawings

PREPARATION OF 1-N-[ω-AMINO-α-HYDROXYALKANOYL]AMINO-GLYCOSIDE POLYSILYLATED ANTIBIOTICS AND PRODUCTS OBTAINED THEREFROM

CROSS-REFERENCE TO RELATED APPLICATION

This application is a continuation of our co-pending application Ser. No. 33,912, filed Apr. 27, 1979, now abandoned, which is a continuation-in-part of our prior, co-pending application Ser. No. 896,430, filed Apr. 14, 1978 now abandoned, which was a continuation-in-part of our prior co-pending application Ser. No. 791,806, filed Apr. 28, 1977, and now abandoned.

SUMMARY OF THE INVENTION

This invention relates to a process for the preparation of 1-N-[ω-amino-α-hydroxyalkanoyl]aminoglycoside antibiotics having the formula

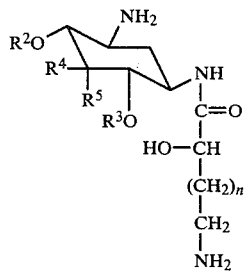

I wherein n is an integer of from 0 to 4; $R^2$ is a substituted hexopyranosyl ring as hereinafter defined; $R^3$ is hydrogen or a substituted hexopyranosyl ring as hereinafter defined; $R^4$ is hydrogen, hydroxy or a pentofuranosyl ring as hereinafter defined; and $R^5$ is hydrogen or hydroxy; provided that, when $R^3$ is other than hydrogen, one of $R^4$ and $R^5$ is hydrogen and the other is hydroxy; and provided that, when $R^3$ is hydrogen, $R^5$ is hydrogen and $R^4$ is a substituted pentofuranosyl ring.

The process involves reacting a polysilylated aminoglycoside prepared from an aminoglycoside of Formula XIV

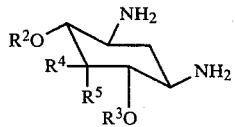

XIV containing from 0 to 3 conventional non-silyl amino-blocking groups on amino groups other than the C-1 amino group, in a substantially anhydrous organic solvent, with an acylating derivative of an acid of the formula

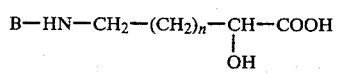

XIII in which B is a conventional amino-blocking group and n is as described above. All blocking groups are then removed by conventional means to produce the desired compound of Formula I.

DESCRIPTION OF THE PRIOR ART

The aminoglycosides are a well-known class of antibiotics and have been widely described in the literature. An excellent review article is that entitled "Structures and Syntheses of Aminoglycoside Antibiotics" by Sumio Umezawa, in Advances in Carbohydrate Chemistry and Biochemistry, 30, 111-182, Academic Press, N.Y. (1974). This review article (and references cited therein) also discusses many known 1-N-(acyl)aminoglycoside antibiotics such as the 1-N-[L-(−)-γ-amino-α-hydroxybutyryl] derivatives of kanamycin A, kanamycin B, 3′,4′-dideoxykanamycin B, tobramycin, paromomycin I, ribostamycin, 3′,4′-dideoxyribostamycin and lividomycin A.

U.S. Pat. No. 4,029,882 discloses 1-N-acyl derivatives of gentamicins A, B, $B_1$, $C_1$, $C_{1a}$, $C_2$, $C_{2a}$ and $X_2$, sisomicin, verdamicin, mutamicins 1, 2, 4, 5 and 6, and antibiotics G-418, 66-40B, 66-40D, JI-20A JI-20B and G-52, wherein the acyl groups are derived from a straight, branched or cyclic alkyl group containing from 1 to 8 carbon atoms, which may contain an amino or hydroxy substituent, or both an amino and a hydroxy substituent. The compounds are prepared by acylating a partially neutralized acid addition salt of the antibiotic with an acylating derivative of the desired side-chain acid.

U.S. Pat. No. 4,055,715 discloses the 1-N-[L-(−)-γ-amino-α-hydroxybutyryl] derivative of the aminoglycoside XK-62-2, and the process for its preparation by acylating XK-62-2 having its 2′-amino or 2′- and 6′-amino moieties protected by a known amino-protecting group (such as the carbobenzyloxy group), with an acylating derivative of L-(−)-γ-amino-α-hydroxybutyric acid (such as its N-hydroxysuccinimide ester).

U.K. Pat. No. 1,500,218 discloses the D-, L-, and D,L-forms of 1-N-[β-ammino-α-hydroxypropionyl]XK-62-2 and its preparation by substantially the same process as described in U.S. Pat. No. 4,055,715.

U.K. Pat. No. 1,499,041 discloses 1-N-[L-(−)-γ-amino-α-hydroxybutyryl)-6′-N-alkykanamycin] A wherein the 6′-N-alkyl group contains from 1 to 4 carbon atoms. The compounds are prepared inter alia by reacting a 6′-N-alkylkanamycin A (either unprotected or having its 3- or 3″-amino group protected with a conventional amino-blocking group) with an acylating derivtive of L-(−)-γ-amino-αhydroxybutric acid.

U. K. Pat. No. 1,475,481 discloses 1-N-acyl derivatives of 6′-N-methyl-3′,4′-dideoxykanamycin B, wherein the acyl groups may be in the L- or D,L-form and have the formula

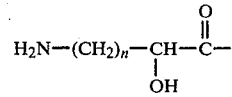

in which n is 1, 2 or 3. The compounds are prepared by acylating the aminoglycoside (having its 6′-amino, and optionally its 2′-amino moiety, protected by a conventional aminoblocking group) with an acylating agent containing the above acyl group, e.g. its N-hydroxysuccinimide ester.

South African Pat. No. 77/1944 discloses inter alia a process for the preparation of 1-N-(lower)alkanoyl derivatives of kanamycin A and B, in which the alkanoyl groups may be substituted by hydroxy and/or amino. The process involves acylation of kanamycin A or B in which the 3-amino moiety of kanamycin A or B and the 2'-amino moiety of kanamycin B (and optionally the 6'-amino moiety of each antibiotic) is protected with a conventional amino-blocking group. Acylation is achieved in a conventional manner, such as by use of the N-hydroxysuccinimide ester of the acylating acid.

U.S. Pat. No. 3,974,137 discloses and claims a process for preparing 1-[L-(−)-γ-amino-α-hydroxybutyryl]-kanamycin A which comprises reacting 6'-carbobenzyloxykanamycin A with at least three moles of benzaldehyde, a substituted benzaldehyde or pivaldehyde, to produce 6'-N-carbobenzyloxykanamycin A containing Schiff base moieties on the 1,3 and 3" -positions, acylating this tetra-protected kanamycin A derivative with the N-hydroxysuccinimide ester of L-(∓)-γ-benzyloxycarbonylamino-γ-hydroxybutyric acid, and subsequently removing the protecting groups.

Trimethylsilyl derivatives of various aminoglycoside antibiotics are known. They have been prepared to impart volatility to these relatively non-volatile compounds, for purposes of gas chromatography and mass spectroscopy analyses.

Bunseki Kagaku, 22, 405–410 (1973) [Chemical Abstracts, 79, 83498y (1973)] reports gas chromatography and mass spectroscopy analyses of trimethylsilyl derivatives of kanamycin A, kanamycin B and neomycin B. These were persilylated compounds in which all hydroxy and amino groups were silylated.

In J. Am. Chem. Soc., 89, 3364-5 (1967), D. C. DeJongh et al. report on mass spectrometric structural analysis studies conducted on the per(N-acetyl)-per(O-trimethylsilyl) derivatives of paromomycin and paromomycin II.

In Tetrahedron Letters, No. 46, pp 4009-12 (1974), T. Takamoto and S. Hanessian, report the conversion of paromomycin into a pseudotrisaccharide by elimination of the diaminohexose unit, and the confirmation of its structure by high resolution mass spectroscopic analysis of its per (N-acetyl)-per(O-trimethylsilyl) derivative. On pages 4013-6 of the same volume, T. Ogawa et al. report the preparation of a positional isomer of the above pseudotrisaccharide and confirmation of its structure by high resolution mass spectroscopy of its per(N-acetyl)-per(O-trimethylsilyl) derivative.

In the Journal of Antibiotics, 28, 522-9 (1975) P. W. K. Woo describes the synthesis of 5"-amino-3',4', 5"-trideoxybutirosin and report that its structure is consistent with the mass spectrum of its per(N-acetyl)-per(O-trimethylsilyl) derivative.

In the Journal of Antibiotics, 26, 374-385 (1973), S. Inouye et al. report the isolation of a new member of the destomycin group of aminoglycosides from a culture broth of Streptomyces eurocidicus SS-56. Its structure was elucidated by means of gas chromatography of its per (trimethylsilyl) derivative and mass spectroscopy of the per(O-trimethylsilyl)N-salicylidene Schiff base derivative.

In the Journal of Antibiotics, 26, 784-6 (1973), M. Kojima and A. Satoh report the semi-synthesis of several aminoglycoside antibiotics (e.g. ribostamycin and 3',4'-dideoxyribostamycin) by the addition of deoxystreptamine or neamine analogs to fermentation broths of deoxystreptamine-negative mutants of Streptomyces ribosidifucus and Streptomyces kanamyceticus. Their structures were eluciated by mass spectroscopy of their N-acetyl-O-trimethylsilyl derivatives.

In Analytical Chemistry, 42, 1661-3 (1970), K. Tsuji and J. H. Robertson describe a method for the separation and determination of the kanamycins and paromomycins by silylation and gas chromatography of the per(trimethylsilyl) derivatives.

In Proc. Nat. Acad. Sci., 63, 198-204 (1969), W. T. Shier et al. report the preparation of hybrimycins A1, A2, B1 and B2 by fermentation of a mutant of Streptomyces fradiae, and mass spectroscopic analysis of their N-acetyl-per(O-trimethylsilyl) derivatives.

In the Journal of Antibiotics, 26, 790-3 (1973), T. P. Culbertson et al. report the preparation of 5"-amino-5"-deoxybutirosins A and B from butirosins A and B. The first steps in the synthesis involved:

(1) partially N-trifluoroacetylating butirosin base by refluxing in a mixture of methanol and ethyl trifluoroacetate,
(2) evaporating to dryness, dissolving the residue in pyridine, treating it with hexamethyldisilazane and trimethylchlorosilane, then cooling to <10° C. and treating it with trifluoroacetic anhydride,
(3) evaporating to dryness and hydrolyzing the residue in a 2:1 mixture of ethanol and 2 N acetic acid at reflux, to give tetra[N-(trifluoroacetyl)]butirosin.

The final products of the synthetic scheme, 5"-amino-5"-deoxybutirosins A and B, also were reacted according to the above three steps to give penta[N-(trifluoroacetyl)]-5"-amino-5"-deoxybutirosins A and B. Although this publication discloses the acylation of a trimethylsilylated (and partially acylated) aminoglycoside antibiotic, the result in each instance is complete acylation of all primary amino groups in the molecule (four in the starting bitirosin and five in the product). The process of the present invention substantially eliminates polyacylation and provides a high degree of selectivity of acylation in the desired 1-N-position.

J. J. Wright et al., in The Journal of Antibiotics, 29, 714-719 (1976), describe a general procedure for the selective 1-N-acylation of the gentamicin-sisomicin class of aminoglycosides. They report that selectivity in the site of acylation is Ph dependent and that the C-1 amino group is the most reactive toward acylation when the amino groups of the molecule are almost completely protonated. These conditions are achieved by the addition of one equivalent of a tertiary amine base to a solution of the fully neutralized acid addition salt. Although these workers obtained 1-N-selectivity in the acylation of gentamicin $C_{1a}$, sisomicin and verdamicin, they reported that little selectivity was observed in the acylation of highly hydroxylated aminoglycosides such as gentamicin B and kanamycin A.

U.K. Pat. No. 1,460,039 discloses a process for the preparation of various deoxyaminoglycoside antibiotics by halogenating a phosphorylated aminoglycoside (one in which the hydroxy group to be removed has been converted to a phosphonoxy group), to produce the corresponding aminoglycoside in which the hydroxy group has been converted to halogen, and reducing the halogen compound to produce the corresponding deoxyaminoglycoside. Before halogenating the phosphorylated aminoglycoside, all of its functional groups are preferably protected by means of silyl or acyl groups.

DETAILED DESCRIPTION

The present invention provides an improved process for the preparation of 1-N-[ω-amino-α-hydroxyalkanoyl]aminoglycoside antibiotics. The use of a polysilylated aminoglycoside as a starting material gives high solubility in the organic solvent system, thus permitting reaction at high concentrations. Although the reaction is usually conducted in solutions containing about 10–20% polysilylated aminoglycoside starting material, excellent results have been obtained at concentrations of about 50% W/V (e.g. 50 gms./100 ml. of solution).

As with prior art processes, the present process gives a mixture of acylated products, and the desired 1-N-acyl product is separated from the other products by chromatography. However, the position of substitution is much more selective when utilizing the present invention, thereby giving smaller amounts of undesired products which both increases the yield of desired product and simplifies chromatographic purification. Thus, in preparing 1-[L-(−)-γ-amino-α-hydroxybutryl]kanamycin A (BB-K8) by various prior art procedures, there is typically also produced the 3″-N-acylated product (BB-K11), the 3-N-acylated product (BB-K29), the 6′-N-acylated product (BB-K6) and polyacylated material, as well as unreacted kanamycin A. In commercial production of BB-K8 by acylation of 6′-N-carbobenzyloxykanamycin A in an aqueous medium, followed by removal of the protecting group, we found that about 10% of the desired BB-K8 (2.5 kg. in a 25 kg. batch) usually was lost because of the presence of BB-K11 as a co-product. Any 3″-N-acylated material which was produced caused a loss of about an equal amount of the desired 1-N-acylated product, due to the great difficulty of separating the latter from the former. The selectivity of substitution of the present process is illustrated by the extremely low amount of undesirable 3″-N-acylated product which is produced when preparing BB-K8 by the present process. Typically, no BB-K11 is detected in the reaction mixture.

The present invention provides a process for the preparation of 1-N-[ω-amino-α-hydroxyalkanoyl]aminoglycoside antibiotics of the formula I

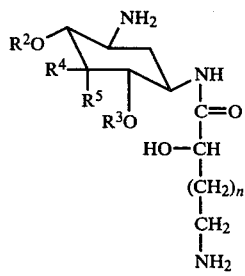

or a pharmaceutically acceptable acid addition salt thereof, wherein n is an integer of from 0 to 4; $R^2$ is a hexopyranosyl ring of the formula

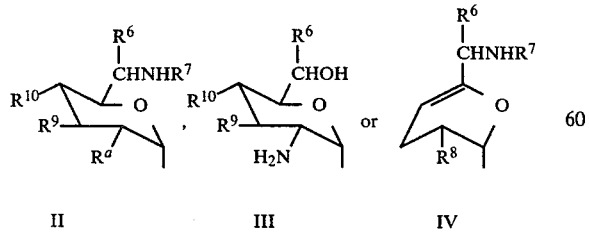

in which $R^6$ is H or $CH_3$, $R^7$ is H or $CH_3$, $R^8$ is OH or $NH_2$, $R^9$ is H or OH and $R^{10}$ is H or OH;

$R^3$ is H or a hexopyranosyl ring of the formula

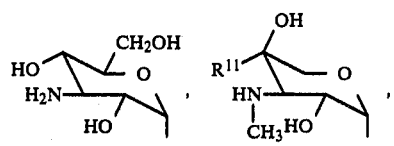

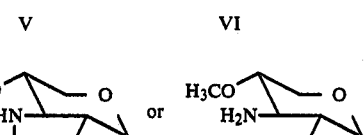

in which $R^{11}$ is H or $CH_3$; $R^5$ is H or OH; and $R^4$ is H, OH or a pentofuranosyl ring of the formula

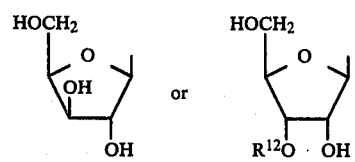

in which $R^{12}$ is H or a hexopyranosyl ring of the formula

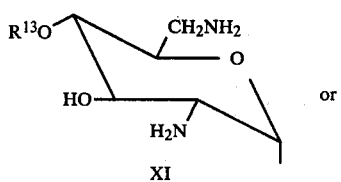

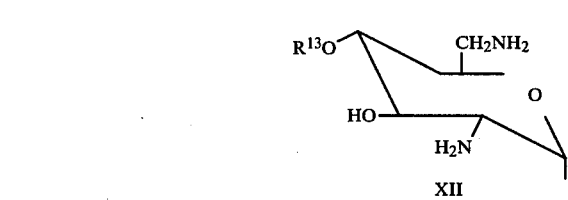

in which $R^{13}$ is H or α-D-mannopyranosyl; provided that, when $R^3$ is other than H, one of $R^4$ and $R^5$ is H and the other is OH; and provided that, when $R^3$ is H, $R^5$ is H and $R^4$ is a pentofuranosyl ring of Formula IX or X; which process comprises reacting a polysilylated aminoglycoside prepared from an aminoglycoside of Formula XIV

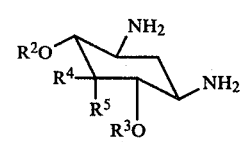

in which $R^2$, $R^3$, $R^4$ and $R^5$ are as defined above, and which contains from 0 to 3 conventional non-silyl amino-blocking groups on amino groups other than the C-1 amino group, in a substantially anhydrous organic solvent, with an acylating derivative of an acid of the formula

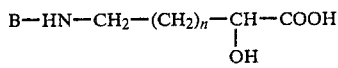

XIII in which B is a conventional amino-blocking group and n is as defined above; and subsequently removing all blocking groups by conventional means.

The amino group of the acylating acid of Formula XIII above must be protected by an amino-blocking group during the acylation reaction. This is normally done by the use of a conventional amino-blocking group. These same conventional amino-blocking groups may be utilized to protect amino groups other than the C-1 amino group of the aminoglycoside. Such conventional blocking groups for the protection of primary amino groups are well known to those skilled in the art. Suitable blocking groups include alkoxycarbonyl groups such as t-butoxycarbonyl and t-amyloxycarbonyl; aralkoxycarbonyl groups such as benzyloxycarbony; cycloalkyloxycarbonyl groups such as cyclohexyloxycarbonyl; haloalkoxycarbonyl groups such as trichloroethoxycarbonyl; acyl groups such as phthaloyl and o-nitrophenoxyacetyl; haloacetyl groups such as trifluroacetyl; and other well-known blocking groups such as 2,4-dinitrophenyl, trityl, benzyl, alkylbenzyl, etc. Another particularly useful class of blocking groups are those of the formula $R^{23}CH=$ or $R^{23}R^{24}C=$ in which $R^{23}$ is aryl or (lower)alkyl, each of which may be substituted by chloro, bromo, fluoro, nitro, (lower)alkyl, or (lower)alkoxy, and $R^{24}$ is —CH$_2$COOCH$_3$, —CH$_2$COOC$_2$H$_5$ or —CH$_2$COCH$_3$; or $R^{23}$ and $R^{24}$, taken together with the carbon atom to which they are attached, represent a cyclopentylidene, cyclohexylidene or cycloheptylidene moiety. These blocking groups, which form a Schiff base with the amino group, are introduced by reaction with the desired aldehyde or ketone, e.g. benzaldehyde, pivaldehyde, methylacetoacetate, acetylacetone or cyclohexanone.

The acylating acid of Formula XIII contains an asymmetric carbon atom and may exist in its (+) or (−) form or as a mixture thereof (the d,1 form), thus producing the corresponding compound of Formula I in which the 1-N-[ω-amino-α-hydroxyalkanoyl] group is in its (+) [or (R)] form or its (−) [or (S)] form, or a mixture thereof. Each such optically active form, and the mixture thereof, is included within the scope of this invention, but the (−) form is preferred.

Acylation of the polysilylated aminoglycoside (with or without from 1 to 3 conventional non-silyl aminoblocking groups on amino groups other than the C-1 amino group) may, in general be conducted in any inert organic solvent in which the starting material has sufficient solubility. These starting materials are highly soluble in most common organic solvents. Suitable solvents include for example, acetone, diethyl ketone, methyl ethyl ketone, heptane, glyme, diglyme, dioxane, toluene, tetrahydrofuran, cyclohexanone, pyridine, methylene chloride, chloroform and carbon tetrachloride. The choice of solvent is dependent on the particular starting materials employed. Ketones, generally, are the preferred solvent. The most advantageous solvent for the particular combination of reactants being utilized can readily be determined by routine experimentation.

Suitable silylating agents for use in preparing the polysilylated aminoglycoside starting materials utilized herein include those of the formula

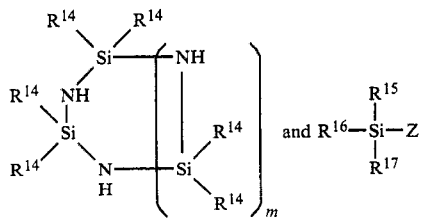

XV            XVI wherein $R^{15}$, $R^{16}$ and $R^{17}$ are selected from the group consisting of hydrogen, halogen, (lower)alkyl, (lower)alkoxy, halo(lower) alkyl and phenyl, at least one of the said $R^{15}$, $R^{16}$ and $R^{17}$ groups being other than halogen or hydrogen; $R^{14}$ is (lower)alkyl, m is an integer of 1 to 2 and Z is selected from the group consisting of halogen and

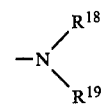

wherein $R^{18}$ is hydrogen or (lower)alkyl and $R^{19}$ is hydrogen, (lower)alkyl or

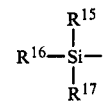

in which $R^{15}$, $R^{16}$ and $R^{17}$ are as defined above.

Specific silyl compounds of Formulas XV and XVI are: trimethylchlorosilane, hexamethyldisilazane, triethylchlorosilane, methyltrichlorosilane, dimethyldichlorosilane, triethylbromosilane, tri-n-propylchlorosilane, methyldiethylchlorosilane, dimethylethylchlorosilane, dimethyl-t-butylchlorosilane, phenyldimethylbromosilane, benzylmethylethylchlorosilane, phenylethylmethylchlorosilane, triphenylchlorosilane, triphenylfluorosilane, tri-o-tolylchlorosilane, tri-p-dimethylaminophenylchlorosilane, N-ethyltriethylsilylamine, hexaethyldisilazane, triphenylsilylamine, tri-n-propylsilylamine, tetraethyldimethyldisilazane, hexaphenyldisilazane, hexa-p-tolyldisilazane, etc. Also useful are hexaalkylcyclotrisilazanes and octa-alkylcyclotetrasilazanes. Other suitable silylating agents are silylamides (such as trialkylsilylacetamides and bistrialkylsilylacetamides), silylureas (such as trimethylsilylurea) and silylureides. Trimethylsilylimidazole also may be utilized.

A preferred silyl group is the trimethylsilyl group and preferred silylating agents for introducing the trimethylsilyl group are hexamethyldisilazane, bis(trimethylsilyl)acetamide, trimethylsilylacetamide and trimethylchlorosilane. Hexamethyldisilazane is most preferred.

Polysilylation of aminoglycosides changes the normal order of activity of the amino groups contained therein. Thus, the 6'-amino group of the kanamycins is the most active. If unprotected kanamycin A or B is acylated, the main products are the 6'-N-acylkanamycins. It is for this reason that prior art procedures for the preparation of 1-N-acylkanamycins required protection of the 6'-N-amino moiety (e.g. with carbobenzyloxy) in order to obtain good yields of the 1-N-acyl product.

However, when acylating the polysilylated kanamycins, the major products are the 1-N-acyl kanamycins. It is believed that this is due to steric effects of adjacent (or nearby) silylated hydroxy groups (as well as adjacent glycoside linkages), which hinder acylation at the normally more active amino groups. But this is only a theoretical explanation and does not form a part of the invention.

Kanamycin B has the formula

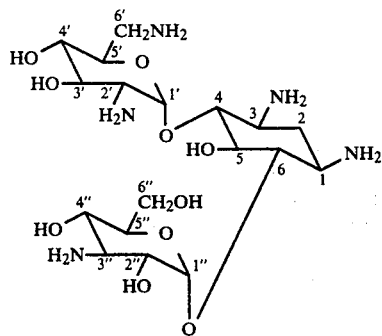

When kanamycin B having all hydroxy groups silylated is considered in light of the above theory of operation, it is seen that the 3''-amino moiety is sterically hindered by the adjacent 2''- and 4''-silylated hydroxy groups. It is believed that it is for this reason that no 3''-acylated product is normally detected when acylating polysilylated kanamycin B (or the structurally similar polysilylated kanamycins A or C), even though troublesome 3''-N-acylated products are obtained in prior art procedures. Similarly, the 6'-amino moiety is hindered by the nearby 4'-and nearby 3'-silylated hydroxy groups. The 2'-amino moiety is hindered by the adjacent 3'-silylated hydroxy and the adjacent glycoside linkage.

Other aminoglycosides which are structurally related to the kanamycins and which, when polysilylated, give primarily the 1-N-acyl product include for example, 3'-deoxykanamycin A, 3'-deoxykanamycin B (tobramycin), the 6'-N-alkylkanamycins A, the 6'-N-alkylkanamycins B, the 3'-deoxy-6'-N-alkylkanamycins A, the 3'-deoxy-6'-N-alkylkanamycins B, gentamicins A, B, $B_1$, and $X_2$, seldomycin factors 1 and 3 and aminoglycosides NK-1001 and NK-1012-1. Each of these, and other structurally similar aminoglycosides, give primarily the 1-N-substituted product when acylated as their polysilylated derivative. Small amounts of 6'-N- and 3-N-substituted products are formed, however, and one of both of these amino moieties may be protected if desired, e.g. with a carbobenzyloxy group.

Another group of aminoglycosides, although otherwise structurally similar to the kanamycin types described above, does not contain either 3'- or 4'-hydroxy groups (i.e. are 3',4'-dideoxy compounds). When polysilylated, these do not sterically hinder the 6'-amino moiety (or 2'-amino moiety, if present), and 6'-N-substituted (or 2',6'-di-N-substituted) compounds are the major products upon acylation. In these aminoglycosides it is necessary to protect the 6'-amino moiety (and 2'-amino moiety, if present) with an amino-blocking group other than silyl (e.g. with carbobenzyloxy) and acylate the polysilylated 6'-N-blocked (or 2',6'-di-N-blocked) aminoglycoside. Aminoglycosides which fall into this group include, for example, 3',4'-dideoxykanamycin A, 3',4'-dideoxykanamycin B, the 6'-N-alkyl-3',4'-dideoxykanamycins A, the 6'-N-alkyl-3',4'-dideoxykanamycins B, gentamicins $C_1$, $C_{1a}$, $C_2$ and $C_{2a}$, aminoglycoside XK-62-2, aminoglycoside 66-40D, verdamicin and sisomicin.

Another class of aminoglycosides are those wherein the glycoside linkage are on the 4- and 5-positions of the deoxystreptamine ring, rather than on the 4- and 6-positions as in the kanamycin type aminoglycosides described above. These may be illustrated by ribostamycin of the formula

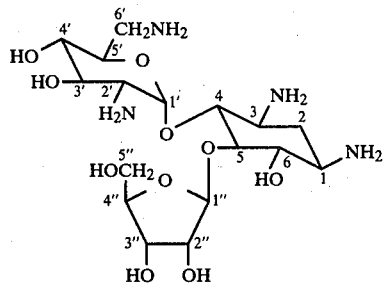

In aminoglycosides of the ribostamycin type, polysilylation hinders the desired 1-N-amino moiety more than the undesired 3-N-amino moiety (the other amino groups being hindered as described above for the kanamycin types). Thus polysilylated antibiotics of the ribostamycin type will form primarily the 3-N-substituted product upon acylation and it therefore is necessary to protect the 3-amino moiety with an amino-blocking group such as carbobenzyloxy, in order to obtain the 1-N-substituted product upon acylation of the polysilylated starting material. Other aminoglycosides which fall into this class include, for example, neomycins B and C, paromomycins I and II, lividomycins A and B, aminoglycoside 2230-C and xylostasin, as well as their 3'-deoxy derivatives. The 6'-N-alkyl and 3'-deoxy-6'-N-alkyl variants of any of the above ribostamycin type antibiotics which contain a 6'-amino group are also included in this class. [Some of the aminoglycosides in this class contain a 6'-hydroxy group rather than a 6'-amino group].

Another group of aminoglycosides are those of the ribostamycin type described above, but which are 3',4'-dideoxy. As with the 3',4'-dideoxykanamycin type aminoglycosides described above, the 2'- and 6'-amino moieties (of those aminoglycosides in this class which contain a 6'-amino moiety) will not be hindered by polysilylation. Accordingly, with compounds such as 3',4'-dideoxyribostamycin, 3',4'-dideoxyneomycins B and C, and 3',4'-dideoxyxylostasin, as well as their 6'-N-alkyl analogs, it is necessary to protect the 2'-, 3- and 6'-amino moieties with an amino-blocking group such as carbobenzyloxy, in order that acylation of the polysilylated starting material will produce primarily the 1-N-acyl product. In those aminoglycosides of this class which contain a 6'-hydroxy group rather than a 6'-amino group (e.g. 3',4'-dideoxyparomomycins I and II and 4'-deoxylividomycins A or B), it is only necessary to protect the 2'-and 3-amino moieties.

When utilizing as a starting material a polysilylated aminoglycoside containing from 1 to 3 conventional non-silyl amino-blocking groups on amino groups other than the C-1 amino group, said starting material may be prepared either by polysilylating the desired N-blocked aminoglycoside or by introducing the desired N-blocking group into the polysilylated aminoglycoside (after partial desilylation by hydrolysis or solvolysis, if necessary).

Methods for the introduction of silyl groups into organic compounds, including certain aminoglycosides, are knwon in the art. The polysilylated aminoglycosides (with or without conventional non-silyl blocking groups on amino moieties other than the C-1 amino group) may be prepared by methods which are known per se, or as described in this specification.

As used herein, the term polysilylated aminoglycoside does not include a persilylated aminoglycoside. Thus, for example, the term polysilylated kanamycin A includes kanamycin A containing from 2 to 10 silyl groups in the molecule [there being a total of 11 sites (4 amino groups and 7 hydroxy groups) which may be silylated]. Similarly, polysilylated kanamycin A containing a single non-silyl amino-blocking group includes the N-blocked kanamycin containing from 2 to 9 silyl groups (and excludes the persilylated compound which would contain 10 silyl groups), while polysilylated kanamycin A containing two non-silyl amino-blocking groups includes the di-N-blocked kanamycin containing from 2 to 8 silyl groups (and excludes the persilylated compound which would contain 9 silyl groups, etc.

The precise number of silyl groups (or their location) present in the polysilylated aminoglycoside starting materials (with or without from 1 to 3 conventional non-silyl amino-blocking groups on amino groups other than the C-1 amino moiety) is not known. We have found that both undersilylation and oversilylation lower the yield of the desired product and increase the yield of other products. In the case of gross under- or oversilylation, little or none of the desired product may be formed. The degree of silylation which will give the greatest yield of the desired product will depend on the particular reactants being used in the acylation step. The most advantageous degree of silylation using any combination of reactants can readily be determined by routine experimentation.

It is believed that the preferred average number of silyl groups in the polysilylated aminoglycoside starting material will usually be between a lower limit of 4 and an upper limit which is equal to one more than the total number of hydroxy groups in the aminoglycoside molecule, and that these upper and lower limits are decreased by one for each non-silyl amino-blocking group present in the aminoglycoside molecule, to a minimum of 2 silyl groups per aminoglycoside molecule. But this explanation is only theory, and is not considered an essential part of the invention.

Polysilylated aminoglycosides containing the desired number of silyl groups may be prepared either by utilizing an amount of silylating agent which is only sufficient to add the desired number of silyl groups or by utilizing excess silylating agent to persilylate the aminoglycoside and then partially desilylating by hydrolysis or solvolysis.

Thus, for example, when preparing 1-N-[L-(−)-γ-amino-α-hydroxybutyryl]kanamycin A by acylating polysilylated kanamycin A with the N-hydroxysuccinimide ester of L-(−)-γ-benzyloxycarbonylamino-α-hydroxybutyric acid in acetone solution, we have found that good yields of the desired product are obtained by utilizing polysilylated kanamycin A which has been prepared by reacting from about 4 to about 5.5 moles of hexamethyldisilazane per mole of kanamycin A. Greater or lesser amounts of hexamethyldisilazane may be utilized, but the yield of desired product in the subsequent acylation step is lowered significantly. In the specific process set forth above we prefer to utilize from about 4.5 to about 5.0 moles of hexamethyldisilazane per mole of kanamycin in order to obtain maximum yield of product in the acylation step.

It will be appreciated that each mole of hexamethyldisilazane is capable of introducing two equivalents of the trimethylsilyl group into kanamycin A or B. Kanamycin A or B each have a total of eleven sites ($NH_2$ and OH groups) which might be silylated, while kanamycin A and B containing a single non-silyl blocking group on an amino moiety other than the C-1 amino group each have a total of 10 such sites, and kanamycin A and B containing two non-silyl amino-blocking groups each contain 9 such sites, etc. Thus, 5.5 moles of hexamethyldisilazane per mole of kanamycin A or B could theoretically completely silylate all OH and $NH_2$ moieties of the kanamycin, while 5.0 moles of hexamethyldisilazane could completely silylate one mole of kanamycin A or B containing a single-non-silyl blocking group on an amino moiety other than the C-1 amino group, and 4.5 moles of hexamethyldisilazane could completely silylate one mole of kanamycin A or B containing two non-silyl amino-blocking groups, etc. However, we believe that such extensive silylation does not take place with these molar ratios during reasonable reaction time periods, although higher degrees of silylation are obtained in a given reaction time when a silylation catalyst is added.

Silylation catalysts greatly accelerate the rate of silylation. Suitable silylation catalysts are well known in the art and include inter alia amine sulfates (which may be the aminoglycoside sulfate), sulfamic acid, imidazole and trimethylchlorosilane. Silylation catalysts generally promote a higher degree of silylation than is required in the process of this invention. However, oversilylated aminoglycosides can be used as starting material if they are first treated with a desilylating agent to reduce the degree of silylation before the acylation reaction is carried out.

Thus, for example, good yields of desired product are obtained when acylating polysilylated kanamycin A prepared using a 5.5:1 molar ratio of hexamethyldisilazane to kanamycin A. However, when kanamycin A silylated with a 7:1 molar ratio of hexamethyldisilazane (or with a 5.5:1 molar ratio in the presence of a silylation catalyst) was acylated in acetone with the N-hydroxysuccinimide ester of L-(−)-γ-benzyloxycarbonylamino-α-hydroxybutyric acid, less than a 1% yield of the desired product was obtained. However, when this same "oversilylated" kanamycin A was acylated with the same acylating agent in acetone solution to which water [21 moles water per mole of kanamycin; 2.5% water (W/V)] had been added as a desilylating agent 1 hour before acylation, a yield of approximately 40% of the desired product was obtained. The same results are obtained if the water is replaced by methanol or other active hydrogen compound capable of effecting desilylation, e.g. ethanol, propanol, butanediol, methyl mercaptan, ethyl mercaptan, phenyl mercaptan, or the like.

Although it is usual to utilize dry solvents when working with silylated materials, we have surprisingly found that, even in the absence of "oversilylation", the addition of water to the reaction solvent prior to acylation often gives equally good yields, and sometimes gives better yields of desired product than in a dry solvent. Thus, for example, in acylation reactions conducted in acetone at the usual concentrations of 10–20% (W/V) of polysilylated kanamycin A, we have found that excellent yields of 1-N-[L-(−)-γ-amino-α-hydroxybutyryl]kanamycin A were obtained when adding up to 28 moles of water per mole of polysilylated kanamycin A; at 20% concentration, 28 moles per mole is approximately 8% water. With other combinations of reactants and solvents, even more water may be tolerated or be beneficial. The acylation reaction may be conducted in solvents containing up to about 40% water, although at such high water concentrations one must utilize short acylation times in order to avoid excessive desilylation of the polysilylated aminoglycoside starting material. Accordingly, as used herein and in the claims, the term "substantially anhydrous organic solvent" is intended to include solvents containing up to about 40% water. A preferred range is up to about 20% water, a more preferred range is up to about 8% water and the most preferred range is up to about 4% water.

Except as described above for solvents containing very high water levels, the duration of the acylation reaction is not critical. Temperatures in the range of about −30° C. to about 100° C. may be used for reaction times ranging from about one hour up to a day or more. The reaction usually proceeds well at room temperature and, for convenience, may be conducted at ambient temperature. However, for maximum yields and selective acylation, we prefer to conduct the acylation at from about 0° to 5°.

Acylation of the 1-amino moiety of the polysilylated aminoglycoside (with or without conventional non-silyl blocking groups on amino moieties other than the C-1 amino group) may be conducted with any acylating derivative of the acid of Formula XIII which is known in the art to be suitable for the acylation of a primary amino group. Examples of suitable acylating derivatives of the free acid include the corresponding acid anhydrides, mixed anhydrides, e.g. alkoxyformic anhydrides, acid halides, acid azides, active esters and active thioesters. The free acid may be coupled with the polysilylated aminoglycoside starting material after first reacting said free acid with N,N'-dimethylchloroforminium chloride [cf. Great Britain 1,008,170 and Novak and Weichet, Experientia XXI, 6, 360 (1965)] or by the use of an N,N'-carbonyldiimidazole or and N,N'-carbonylditrizaole [cf. South African Specification No. 63/2684] or a carbodiimide reagent [especially N,N'-dicyclohexylcarbodiimide, N,N'-diisopropylcarbodiimide or N-cyclohexyl-N'-(2-morpholinoethyl)-carbodiimide: cf. Sheehan and Hess, J.A.C.S., 77, 1967 (1955)], or of an alkynylamine reagent [cf. R. Buijle and H. G. Viehe, Angew. Chem. International Edition, 3, 582 (1964)] or of an isoxazolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DDPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As will be appreciated by those skilled in the art, it sometimes may be desirable or necessary to protect the hydroxyl group of the acylating derivative of the acid of Formula XIII, e.g. when utilizing acylating derivatives such as an acid halide. Protection of the hydroxy group may be accomplished by means known in the art, e.g. by use of a carbobenzyloxy group, by acetylation, by silylation, or the like.

In a preferred embodiment of the invention the acylating derivative of the acid of Formula XIII is an active ester, and preferably its active ester with N-hydroxysuccinimide, N-hydroxy-5-norbornene-2,3-dicarboximide or N-hydroxyphthalimide. In another preferred embodiment the acylating derivative of the acid of Formula XIII is a mixed acid anhydride, and preferably its mixed acid anhydride with pivalic acid, benzoic acid, isobutylcarbonic acid or benzylcarbonic acid.

After the acylation of the polysilylated aminoglycoside is complete, all blocking groups are removed by methods known per se, to yield the desired product of Formula I. The silyl groups, for example, are readily removed by hydrolysis with water, preferably at low pH. Amino-blocking groups on the aminoglycoside molecule (if present) or on the acyl side-chain may also be removed by known methods. Thus, a t-butoxycarbonyl group may be removed by the use of formic acid, a carbobenzyloxy group by catalytic hydrogenation, a 2-hydroxy-1-naphthcarbonyl group by acid hydrolysis, a trichloroethoxycarbonyl group by treatment with zinc dust in glacial acetic acid, the phthaloyl group by treatment with hydrazine hydrate in ethanol under heating, the trifluoroacetyl group by treatment with NH$_4$OH, etc.

Preferred amino-blocking groups useful for protecting amino groups in the aminoglycoside molecule as well as the amino group in the acylating acid of Formula XIII are those of the formulae

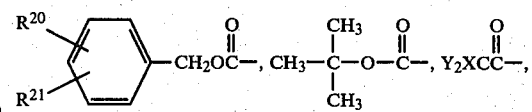

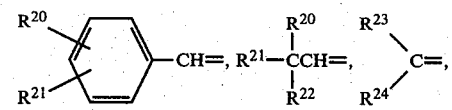

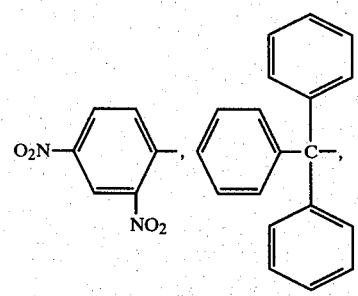

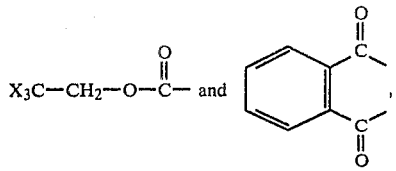

wherein $R^{20}$, $R^{21}$ and $R^{22}$ are alike or different and each is H, F, Cl, Br, $NO_2$, OH, (lower)alkyl or (lower)alkoxy, X is Cl, Br, F or I, Y is H, Cl, Br, F or I, $R^{23}$ is aryl or (lower)alkyl, each of which may be substituted by chloro, bromo, fluoro, nitro, (lower)alkyl, or (lower)alkoxy, and $R^{24}$ is $-CH_2COOCH_3$, $-CH_2COOC_2H_5$ or $-CH_2COOCH_3$; or $R^{23}$ and $R^{24}$, taken together with the carbon atom to which they are attached, represent a cyclopentylidene, cyclohexylidene or cycloheptylidene moiety. A particularly preferred amino-blocking group for use in the aminoglycoside molecule is the carbobenzyloxy group. Particularly preferred amino-blocking groups for use in the acylating acid of Formula XIII are the carbobenzyloxy, trifluoroacetyl and t-butyloxycarbonyl groups.

Some of the compounds of Formula I contain a double bond (i.e. where substituent $R^2$ has the structure IV). These are compounds derived from aminoglycosides such as sisomicin, verdamicin, G-52, 66-40B and 66-40D. When utilizing such compounds, those skilled in the art will appreciate that any reductive techniques which would reduce the double bond should be avoided. Thus, for example, amino-blocking groups which are removable by hydrolysis or by means of an alkali metal in liquid ammonia should be utilized, so as to avoid reduction of the double bond, as would occur with such techniques as catalytic hydrogenolysis.

Yields of product were determined by various methods. After removal of all blocking groups and chromatography on a CG-50 ($NH_4+$) column, the yield could be determined by isolation of the crystalline solid from the appropriate fractions or by microbiological assay (turbidimetric or plate) of the appropriate fractions. Another technique which we utilized was high performance liquid chromatography of the unreduced acylation mixture, i.e. the aqueous solution obtained after hydrolysis of the silyl groups and removal of organic solvent but before hydrogenolysis to remove the remaining blocking group(s). This assay was not a direct assay for the final product, but for the corresponding N-blocked compounds.

The instrument utilized was a Waters Associates ALC/GPC 244 high pressure liquid chromatograph with a Waters Associates Model 440 absorbance detector and a 30 cm × 3.9 mm i.d. μ-Bondapak C-18 column, under the following conditions:

Mobile Phase:
 25% 2-propanol
 75% 0.01 M sodium acetate pH 4.0
Flow Rate: 1 ml./minute
Detector: UV at 254 nm.
Sensitivity: 0.04 AUFS
Diluent: DMSO
Injected Amount: 5 μl
Concentration: 10 mg./ml.

Chart speed varied, but 2 minutes/inch was typical. The above conditions gave UV traces with peaks which were easy to measure quantitatively. The results of the above analyses are referred to in the specification as HPLC assays.

In order to avoid the repetition of complex chemical names, the following abbreviations are sometimes utilized in this specification.
 AHBA: L-(−)-γ-amino-α-hydroxybutyric acid
 BHBA: N-Carbobenzyloxy derivative of AHBA
 HONB: N-hydroxy-5-norbornene-2,3-dicarboximide
 NAE: (or BHBA-'ONB'): N-hydroxy-5-norbornene-2,3-dicarboximide activated ester of BHBA
 HONS: N-hydroxysuccinimide
 SAE: (or BHBA-'ONS'): N-hydroxysuccinimide activated ester of BHBA
 DCC: dicyclohexylcarbodiimide
 DCU- dicyclohexylurea
 HMDS: hexamethyldisilazane
 BSA: bis(trimethylsilyl)acetamide
 MSA: trimethylsilylacetamide
 TFA: trifluoroacetyl
 t-BOC: tert. butyloxycarbonyl "Dicalite" is a trademark of the Great Lakes Carbon Corporation for diatomaceous earth.

"Amberlite CG-50" is a Trademark of the Rohm & Haas Co. for the chromatographic grade of a weakly acid cationic exchange resin of the carboxylic-polymethacrylic type.

Amberlite 1RA-410 is a Trademark of the Rohm & Haas Co. for the chromatographic grade of a strongly basic anion exchange resin of the styrene-divinylbenzene type.

Diaion HP-10 is a Trademark of Mitsubishi Chemical Industries, Ltd. (Japan) for a chromatographic resin which is a highly porous copolymer of styrene and divinylbenzene.

"μ-Bondapak" is a Trademark of Waters Associates for a series of high performance liquid chromatography columns.

All temperatures herein are given in degrees centigrade.

As used herein, the terms "(lower)alkyl" and "(lower)alkoxy" refer to alkyl or alkoxy groups containing from 1 to six carbon atoms.

As used herein and in the claims, the term "pharmaceutically acceptable acid addition salt" of a compound of Formula I means a mono-, di-, tri-, tetra- (or higher) salt formed by the interaction of one molecule of a compound of Formula I with 1 or more equivalents of a nontoxic, pharmaceutically acceptable acid, depending on the particular compound of Formula I. It will be appreciated that an acid addition salt can be formed at each amino group in the molecule, both in the aminoglycoside nucleus and in the acyl side chain. Included among these acids are acetic, hydrochloric, sulfuric, maleic, phosphoric, nitric, hydrobromic, ascorbic, malic and citric acid, and those other acids commonly used to make salts of amine-containing pharmaceuticals.

Most of the aminoglycosides used as starting materials in the present invention are known in the art. Any individual aminoglycoside which is not known per se (e.g. a not previously described 6'-N-methyl derivative of a known aminoglycoside) may readily be prepared by methods well-known in the art for the preparation of analogous compounds.

The compounds of Formula I produced by the present invention are active against Gram-positive and Gram-negative bacteria and are used analogously to other known aminoglycosides. Many of the compounds of Formula I are known per se.

In another aspect the present invention provides polysilylated aminoglycosides prepared from a compound of Formula XIV or polysilylated aminoglycosides prepared from a compound of Formula XIV containing from 1 to 3 conventional non-silyl amino-blocking groups on amino moieties other than the C-1 amino group.

DESCRIPTION OF THE PREFERRED EMBODIMENTS

EXAMPLE 1

Preparation of
1-N-[L-(−)-γ-Amino-α-hydroxybutyryl]kanamycin A (BB-K8) by Selective Acylation of Poly(trimethylsilyl) 6′-N-Carbobenzyloxykanamycin A in Anhydrous Diethyl Ketone 6′-N-Carbobenzyloxykanamycin A (15 g., 24.24 m. moles) was slurried in 90 ml. of dry acetonitrile and heated to reflux under a nitrogen atmoshere. Hexamethyldisilazane (17.5 g., 108.48 m. moles) was added slowly over 30 minutes, and the resulting solution was refluxed for 24 hours. After removal of the solvent in vacuo (40°) and complete drying under vacuum (10 mm), 27.9 g. of a white, amorphous solid was obtained [90.71% calculated as 6′-N-Carbobenzyloxykanamycin A (Silyl)$_9$].

This solid was dissolved in 150 ml. of dry diethyl ketone at 23°. L-(−)-γ-benzyloxycarbonylamino-α-hydroxybutyric acid N-hydroxy-5-norbornene-2,3-dicarboximide ester (NAE) (11.05 g., 26.67 m. moles) dissolved in 100 ml. of dry diethyl ketone at 23° was added slowly with good agitation over ½ hour. The solution was stirred at 23° for 78 hours. The yellow, clear solution (pH 7.0) was diluted with 100 ml. of water. The pH of the mixture was adjusted to 2.8 (3 N HCl) and stirred vigorously at 23° for 15 minutes. The aqueous phase was separated, and the organic phase was extracted with 50 ml. of pH 2.8 water. The combined aqueous fractions were washed with 50 ml. of ethyl acetate. The solution was placed in a 500 ml. Parr bottle, together with 5 g. of 5% palladium on carbon catalyst (Engelhard) and reduced at 50 psi H$_2$ for 2 hours at 23°. The mixture was filtered through a pad of Dicalite which was then washed with an additional 30 ml. of water. The colorless filtrate was concentrated in vacuo (40°-45°) to 50 ml. The solution was charged on a 5×100 cm CG-50 (NH$_4$+) ion exchange column. After washing with 1000 ml. of water, unreacted kanamycin A, 3-[L-(−)-γ-amino-α-hydroxybutyryl]kanamycin A (BB-K29) and BB-K8 were eluted with 0.5 N ammonium hydroxide. Polyacyl material was recovered with 3 N ammonium hydroxide. Bioassay, thin layer chromatography and optical rotation were used to monitor the progress of elution. The volume and observed optical rotation of each fraction of eluate, as well as the weight and percent yield of solid isolated from each fraction by evaporation to dryness, are summarized below:

| Material | Volume (ml) | α 578 | Weight (gms.) | % Yield |
|---|---|---|---|---|
| Kanamycin A | 1000 | +0.115 | 0.989 | 9.15 |
| BB-K29 | 1750 | +0.24 | 4.37 | 32.0 |
| BB-K8 | 2000 | +0.31 | 6.20 | 47.4 |
| Polyacyls | 900 | +0.032 | 0.288 | 2.0 |

The spent diethyl ketone layer was shown by high performance liquid chromatography to contain an additional 3-5% BB-K8.

The crude BB-K8 (6.20 gms.) was dissolved in 20 ml. of water and diluted with 20 ml. of methanol, and 20 ml. of isopropanol was added to induce crystallization. There was obtained 6.0 gms. (45.8%) of crystalline BB-K8.

EXAMPLE 2

Preparation of
1-N-[L-(−)-γ-Amino-α-hydroxybutyryl]kanamycin A (BB-K8) by Selective Acylation of Poly(trimethylsilyl) Kanamycin A, Using In Situ Blocking A. Poly(trimethylsilyl) Kanamycin A Kanamycin A free base (18 g. activity, 37.15 m. moles) was slurried in 200 ml. of dry acetonitrile and heated to reflux. Hexamethyldisilazane (29.8 g., 184.6 m. moles) was added over 30 minutes and the mixture was stirred at reflux for 78 hours to give a light yellow clear solution. Removal of the solvent under vacuum left an amorphous solid residue (43 gm., 94%) [calculated as kanamycin A (silyl)$_{10}$].

B. 1-N-[L-(−)-γ-Amino-α-hydroxybutyryl]kanamycin A p-(Benzyloxycarbonyloxy)benzoic acid (5.56 g., 20.43 m. moles) was slurried in 50 ml. of dry acetonitrile at 23°. N,O-bis-Trimethylsilyl acetamide (8.4 g., 41.37 m. mole) was added with good stirring. The solution was held for 30 minutes at 23°, and then added over 3 hours with vigorous stirring to a solution of poly(trimethylsilyl)kanamycin A (21.5 g., 17.83 m. mole, calculated as the (silyl)$_{10}$ compound) in 75 ml. of dry acetonitrile at 23°. The mix was stirred for 4 hours, the solvent was removed in vacuo (40°), and the oily residue was dissolved in 50 ml. of dry acetone at 23° C.

L-(−)-γ-benzyloxycarbonylamino-α-hydroxybutyric acid N-hydroxy-5-norbornene-2,3-dicarboximide ester (NAE) (8.55 g., 20.63 m. moles) in 30 ml. of acetone was added to the above solution over a period of 5 minutes. The mixture was held at 23° C. for 78 hours. The solution was diluted with 100 ml. of water and the pH (7.0) lowered to 2.5 (6 N HCl). The mixture was placed in a 500 ml. Parr bottle together with 3 g. of 5% palladium on carbon catalyst (Engelhard) and reduced at 40 psi H$_2$ for 2 hours at 23°. The mixture was filtered through a pad of diatomaceous earth which was then washed with 20 ml. of water. The combined filtrate and washings (168 ml.) were determined by microbiological assay against *E. coli* to contain approximately 11,400 mcg/ml. (19% yield) of BB-K8.

EXAMPLE 3

Preparation of
1-N-[L-(−)-γ-Amino-α-hydroxybutyryl]kanamycin A (BB-K8) by Selective Acylation of Poly(trimethylsilyl)Kanamycin A A. Poly(trimethylsilyl) Kanamycin A A suspension of 10 g. (20.6 m. moles) kanamycin A in 100 ml. of dry acetonitrile and 25 ml. (119 m. moles) 1,1,1,3,3,3-hexamethyldisilazane was refluxed for 72 hours. A clear light yellow solution resulted. The solution was stripped to dryness in vacuo at 30°-40° C. There was obtained 21.3 g. of poly(trimethylsilyl)

Kanamycin A as a light tan amorphous powder [85% yield calculated as kanamycin A (silyl)$_{10}$].

B. 1-N-[L-(—)-γ-Amino-α-hydroxybutyryl]kanamycin A

To a solution of 2.4 g. (2.0 m. moles) of poly(trimethylsilyl) Kanamycin A in 30 ml. of dry acetone was added slowly 2.0 m. moles of L-(—)-γ-benzyloxycarbonylamino-α-hydroxybutyric acid N-hydroxy-5-norbornene-2,3-dicarboximide ester (NAE) in 10 ml. of dry acetone at 0°–5° C. The reaction mixture was stirred at 23° C. for a week and then stripped to dryness in vacuo at a bath temperature of 30°–40° C. Water (60 ml.) was then added to the residue, followed by 70 ml. of methanol to obtain a solution. The solution was acidified with 3 N HCl to pH 2.0 and then reduced at 50 psi H$_2$ for 2 hours, using 500 mg of 5% palladium on carbon catalyst. The material was filtered, and the combined filtrate and washings were determined by microbiological assay against *E. coli* to contain a 29.4% yield of BB-K8.

EXAMPLE 4

Preparation of BB-K8 by Acylation of Poly(trimethylsilyl) 6'-N-Cbz Kana A in Tetrahydrofuran With the Mixed Acid Anydride of Pivalic Acid and BHBA A. Preparation of Mixed Anhydride BHBA (5.066 gm., 20.0 m moles), BSA (4.068 gm., 20.0 m moles) and triethylamine (2.116 g, 22.0 m moles) were dissolved in 200 ml. of sieve dried tetrahydrofuran. The solution was refluxed for 2¼ hours and then chilled to —10° C. Pivaloyl chloride (2.412 gm., 20.0 m moles) was added over a period of 2–3 minutes, with stirring, and stirring was continued for 2 hours at —10° C. The temperature was then allowed to climb to 23° C.

B. Acylation of Poly(trimethylsilyl) 6'-N-Cbz Kana A

Poly(trimethylsilyl) 6'-N-Cbz Kana A prepared as in Example 1 (5.454 gm., 4.97 m moles, calculated as 6'-Cbz Kana A (silyl)$_9$) was dissolved in 50 ml. dry (molecular sieve) tetrahydrofuran at 23° C. One-half of the solution of mixed anhydride prepared in step A, above, (10.0 m moles) was added over a period of twenty minutes, with stirring, and stirring was continued for 7 days.

Water (100 ml.) was then added to the reaction mixture, and the pH (5.4) was adjusted to 2.0 with 3 M H$_2$SO$_4$. Stirring was continued for 1 hour and the solution was extracted with ethyl acetate. Polyacylated material began to crystallize, so the reaction mixture was filtered. After drying over P$_2$O$_5$, the recovered solids weighed 0.702 gms. The extraction of the reaction mixture was continued for a total of 4×75 ml. of ethyl acetate, after which the excess ethyl acetate was stripped from the aqueous layer. An aliquot of the aqueous solution was subjected to assay by HPLC. The resulting curve indicated a 26.4% yield of di-Cbz BB-K8.

The aqueous layer was then hydrogenated in a Parr apparatus at 50 p.s.i. H$_2$ pressure for two hours, using 0.5 gm. 10% Pd on carbon catalyst. The material was filtered, and the combined filtrate and washings were determined against *E. coli* to contain a 31.2% yield of BB-K8. BB-K8/BB-K29 ratio approximately 9–10/1; traces of polyacyl and unreacted Kana A present.

EXAMPLE 5

Preparation of BB-K8 by Acylation of Poly(trimethylsilyl) 6'-N-Cbz Kana A in Acetone with the Mixed Anhydride of BHBA and Isobutylcarbonic Acid A. Preparation of Mixed Anhydride BHBA (1,267 gm., 5.0 m moles) and N-trimethylsilylacetamide (MSA) (1.313 gm., 10.0 m moles) in 20 ml. of sieve dried acetone was stirred at 23° C., and triethylamine (TEA) (0.70 ml., 5.0 m moles) were added. The mixture was refluxed under a N$_2$ atmosphere for 2½ hours. The mixture was cooled to —20° C. and isobutylchloroformate (0.751 gm., 0–713 ml., 5.50 m moles) was added. Triethylamine hydrochloride immediately began to separate. The mixture was stirred for 1 hour at —20° C.

B. Acylation

Poly(trimethylsilyl) 6'-N-Cbz Kana A prepared as in Example 1 (6.215 gm., 4.9 m moles, calculated as the (silyl)$_9$ compound) was dissolved in 20 ml. of sieve dried acetone, with stirring, at 23° C. The solution was cooled to —20° C. and the cold mixed anhydride solution from step A was slowly added over a period of 30 minutes. The reaction mixture was stirred for an additional 1½ hours at —20° C. and then for 17 hours at 23° C. The reaction mixture was then poured into 150 ml. of water at 23° C. with stirring, the pH (7.75) was adjusted to 2.5 with 3 N HCl, and stirring was continued for 15 minutes. Acetone was then stripped in vacuo at 40° C. An aliquot of the resulting aqueous solution was subjected to assay by HPLC. The resulting curve indicated a 34.33% yield of di-Cbz BB-K8.

The main portion of the aqueus solution was reduced at 50 p.s.i. H$_2$ pressure at 23° C. for 3¼ hours, utilizing 2.0 gms of Pd/C catalyst. The catalyst was removed by filtration and the combined filtrate and washings were determined by microbiological assay against *E. coli* to contain a 35.0% yield of BB-K8.

EXAMPLE 6

Preparation of BB-K8 by Acylation of Poly(trimethylsilyl) 6'-N-Cbz Kana A in Anhydrous Cyclohexanone For Varying Times.

A. Poly(trimethylsilyl) 6'-N-Cbz Kana A prepared as in Example 1 (2.537 gm., 2.0 m moles, calculated as 6'-N-Cbz Kana A (silyl)$_9$) in 300 ml. dry cyclohexanone was acylated for 20 hours at 23° C. with an NAE solution in dry cyclohexanone (10.8 ml. of 0.1944 m mole/ml. solution, 2.10 m mole). The reaction mixture was then added to 150 ml. of water, with stirring, and the pH (5.6) was adjusted to 2.5 with 3 N HCl. The cyclohexanone was stripped in vacuo at 40° C. and an aliquot of the remaining aqueous phase was taken for assay by HPLC. The main portion of the aqueous phase was reduced under 50 p.s.i. H$_2$ pressure for 3 hours at 23° C., using 1.0 gm of 10% Pd/C catalyst. The catalyst was removed by filtration and the combined filtrate and washings were assayed microbiologically for BB-K8.

B. Reaction A, above, was repeated, except that the acylation was continued for 115 hours instead of 20 hours.

| | Yields | | |
|---|---|---|---|
| | HPLC Assay | Microbiological Assay (BB-K8) | |
| | (di-Cbz BB-K8) | Turbidimetric | Plate |
| Reaction A | 49.18% | 42.87% | 39.16% |
| Reaction B | 56.17% | 55.39% | 38.45% |

EXAMPLE 7

Preparation of BB-K8 by Acylation of Poly(trimethylsilyl) 6′-N-Cbz Kana A in Anhydrous Tetrahydrofuran For Varying Times A. Example 6 A was repeated except that dry tetrahydrofuran was utilized as solvent instead of dry cyclohexanone.

B. Example 6 B was repeated except that dry tetrahydrofuran was utilized as solvent instead of dry cyclohexanone.

| | Yields | | |
|---|---|---|---|
| | HPLC Assay | Microbiological Assay (BB-K8) | |
| | (di-Cbz BB-K8) | Turbidimetric | Plate |
| Reaction A | 29.27% | 28.34% | 28.18% |
| Reaction B | 33.39% | 21.52% | 28.63% |

EXAMPLE 8

Preparation of BB-K8 by Acylation of Poly(trimethylsilyl) 6′-N-Cbz Kana A in Anhydrous Dioxane For Varying Times A. Example 6 A was repeated except that the acylation was continued for 44 hours utilizing dry dioxane as the solvent.

B. Example 6 B was repeated except that the acylation was continued for 18 ½ hours utilizing dry dioxane as the solvent.

| | Yields | | |
|---|---|---|---|
| | HPLC Assay | Microbiological Assay (BB-K8) | |
| | (di-Cbz BB-K8) | Turbidimetric | Plate |
| Reaction A | 39.18% | 43.27% | 33.36% |
| Reaction B | 42.82% | 22.55% | 33.37% |

EXAMPLE 9

Preparation of BB-K8 by Acylation of Poly(trimethylsilyl) 6′-N-Cbz Kana A in Anhydrous Diethyl ketone at 75° C.

To a stirred solution of poly(trimethylsilyl) 6′-N-Cbz Kana A prepared as in Example 1 (2.537 gm., 2.0 m moles, calculated as 6′-N-Cbz Kana A $(silyl)_9$) in 32 ml. sieve dried diethyl ketone at 75° C. was added a solution of NAE (10.8 ml. of 0.1944 m moles/ml. of diethyl ketone, 2.10 m moles) over a period of 15 minutes. Stirring was continued at 75° C. for an additional 3 hours after which the mixture was poured into 150 ml. of water. The pH was adjusted to 2.8 with 3 N HCl and the diethyl ketone was stripped in vacuo at 40° C. HPLC assay of an aliquot of the aqueous phase indicated at 39.18% yield of di-Cbz BB-K8.

The main portion of the aqueous phase was reduced under 49.8 p.s.i. $H_2$ pressure for 3 ¼ hours at 23° C., using 1.0 gm of Pd/C catalyst. The catalyst was removed by filtration and the combined filtrate and washings were assayed microbiologically for BB-K8. Turbidimetric assay showed 27.84% yield and Plate assay showed 28.6% yield.

EXAMPLE 10

Preparation of BB-K8 by the Acylation of Poly(trimethylsilyl) Kana A With NAE at 0°–5° After Back Hydrolysis With Water A. Silylation of Kanamycin A Using HMDS With TMCS as Catalyst Kanamycin A (10 gm of 97.6% purity, 20.14 m moles) in 100 ml of sieve-dried acetonitrile was brought to reflux under a nitrogen atmosphere. A mixture of HMDS (22.76 gm, 141 m moles, 7 moles per mole of kanamycin A) and TMCS (1 ml, 0.856 gm, 7.88 m moles) was added to the refluxing reaction mixture over a period of 10 minutes. Reflux was continued for 4-¾ hours and the mixture was then cooled, concentrated in vacuo to a yellow viscous syrup and dried under high vacuum for 2 hours. The yield of product was 23.8 gms (97.9%, calculated as kanamycin A $(silyl)_{10}$).

B. Acylation

Poly(trimethylsilyl) kanamycin A (23.8 gms, 20.14 m moles) prepared in step A above was dissolved in 250 ml of sieve-dried acetone at 23° and then cooled to 0°–5°. Water (3.63 ml, 201.4 m moles, 10 moles per mole of polysilylated kanamycin A) was added, with stirring, and the mixture was allowed to stand under moderate vacuum for 30 minutes. NAE (19.133 m moles, 0.95 moles per mole of polysilylated kanamycin A) in 108.3 ml of acetone was then added over a period of <1 minute. The mixture was stirred at 0°–5° for 1 hour, diluted with water, the pH adjusted to 2.5, and the acetone was then removed in vacuo. The aqueous solution was then reduced at 50 p.s.i. $H_2$ pressure at 23° for 2-½ hours using 2.0 gms of 10% Pd on carbon as a catalyst. The reduced reaction mixture was filtered through Dicalite, concentrated to ca. 100 ml in vacuo at 40° and then charged on CG-50($NH_4^+$) column (6 liters resin, 5×100 cm). It was washed with water and then eluted with 0.6 N-1.0 N-3 N $NH_4OH$. There was obtained 60.25% BB-K8, 4.37% BB-K6, 4.35% BB-K29, 26.47% kanamycin A and 2.18% polyacyls.

EXAMPLE 11

Preparation of BB-K8 by the Acylation of Poly(trimethylsilyl) 6′-N-Cbz Kana A with SAE at 0°–5° After Back Methanolysis A. Silylation of 6′-N-Cbz Kanamycin A 6′-N-Cbz kanamycin A (20.0 gm, 32.4 m moles) in 200 ml of sieve-dried acetonitrile was brought to reflux under a nitrogen atmosphere. HMDS (47.3 ml, 226.8 m moles, 7 moles per mole of 6′-N-Cbz kana A) was added over a 10 minute period and reflux was continued for 20 hours. The mixture was then cooled, concentrated in vacuo, and dried under high vacuum for 2 hours to give 39.1 gms of white amorphous solid (95.4% yield, calculated as 6′-N-Cbz kana A $(silyl)_9$).

B. Acylation

Poly(trimethylsilyl) 6′-N-Cbz kana A (39.1 gm, 32.4 m moles) prepared in step A above was dissolved in 400 ml of dry acetone, with stirring, at 23°. Methanol (6.6 ml, 162 m moles, 5 moles per mole of polysilylated 6′-N-Cbz kana A) was added and the mixture was stirred at 23° for 1 hour under a strong nitrogen purge. The mixture was cooled to 0°-5° and a solution of SAE (11.35 gm, 32.4 m moles) in 120 ml of pre-cooled, dry acetone was added. The mixture was stirred for an additional 3 hours at 0°-5° and then placed in a 4° cold room for 1 week. Water (300 ml) was added, the pH was adjusted to 2.0, the mixture was stirred for 1 hour, and the acetone was then stripped in vacuo. The resultant aqueous solution was reduced at 54.0 p.s.i. $H_2$ pressure for 17 hours at 23° utilizing 3.0 gm of 10% Pd on carbon as catalyst. It was then filtered through Dicalite, concentrated in vacuo to 75-100 ml, charged on a CG-50($NH_4+$) column and eluted with water and 0.6 N $NH_4OH$. There was obtained 52.52% BB-K8, 14.5% BB-K29, 19.6% Kanamycin A and 1.71% polyacyls.

EXAMPLE 12

Preparation of BB-K8 by the Acylation of Poly(trimethylsilyl) Kana A With SAE at 0°-5° After Back Hydrolysis With Water A. Silylation of Kanamycin A With TMCS in Acetonitrile Using Tetramethylguanidine as Acid Acceptor Kanamycin A (4.88 gm, 10.07 m mole) was suspended in 100 ml of sieve-dried acetonitrile with stirring at 23°. To the stirred suspension was added tetramethylguanidine (TMG) (16.234 gm, 140.98 m moles, 14 moles per mole of kanamycin A). The mixture was heated to reflux and TMCS (15.32 gm, 140.98 m moles, 14 moles per mole of kanamycin A) was added over a 15 minute period. A white precipitate of TMG.HCl formed after about one-half of the TMCS had been added. The mixture was cooled to room temperature, concentrated to a tacky residue and dried under high vacuum for 2 hours. The solid was triturated with dry THF (100 ml), and the insoluble TMG.HCl was filtered off and washed with 5×20 ml portions of THF. The combined filtrate and washings were concentrated in vacuo at 40° to a tacky residue and dried under high vacuum for 2 hours. There was obtained 10.64 gms of a light cream tacky residue (87.6% yield, calculated as kanamycin A (silyl)$_{10}$).

B. Acylation

Poly(trimethylsilyl) kanamycin A (10.64 gm, 10.07 m moles) prepared in step A above was dissolved in 110 ml of sieve-dried acetone, with stirring, at 23° and the solution was cooled to 0°-5°. Water (1.81 ml, 100.7 m moles, 10 moles per mole of polysilylated kana A) was added and the solution was stirred for 30 minutes under moderate vacuum. SAE (3.70 gm, 10.57 m moles, 5% excess) in 40 ml of pre-cooled dry acetone was added over a period of <1 minute, and the mixture was stirred for one hour. The mixture was worked up by the general procedure in Example 11B give ca. 50% BB-K8, ca. 10% BB-K29, 5-8% BB-K6, ca. 20% kanamycin A and 5-8% polyacyls.

EXAMPLE 13

Preparation of Poly(triethylsilyl) Kanamycin A Using Triethylchlorosilane With Triethylamine as Acid Acceptor Kanamycin A (5.0 gms of 97.6% purity, 10.07 m moles) was suspended in 100 ml of sieve-dried acetonitrile at 23°. Triethylamine (TEA) (33.8 ml, 24.5 gm, 241.7 m moles) was added and the suspension was brought to reflux. A solution of trichloroethylsilane (23.7 ml, 21.3 gm, 140.98 m moles) in 25 ml dry acetonitrile was added over a 20 minute period. Reflux was continued for an additional 7 hours and the mixture was cooled to room temperature, whereupon long fine needles of TEA.HCl separated out. The mixture was allowed to stand at room temperature for ca. 16 hours, concentrated in vacuo at 40° to a tacky solid and dried for 2 hours under high vacuum to a deep orange tacky solid. The solid was triturated with 100 ml dry THF at 23° and the insoluble TEA.HCl was filtered off, washed with 5×20 ml of THF, and dried to give 16.0 gms of TEA.HCl. The combined filtrate and washings were concentrated in vacuo to a solid and dried under high vacuum for 2 hours. There was obtained 19.3 gms of poly(triethylsilyl) kanamycin A as a deep orange vascous syrup.

EXAMPLE 14

Preparation of Poly(trimethylsilyl) kanamycin A Using bis-Trimethylsilylurea

Kanamycin A (10.0 gm of 99.7% purity, 20.58 m moles) was suspended in 200 ml of sieve-dried acetonitrile, with stirring, at 23°. To the suspension was added bis-trimethylsilylurea (BSU) (29.45 gms, 144.01 m moles, 7 moles per mole of kanamycin), and the mixture was brought to reflux under a nitrogen atmosphere. Reflux was continued for 17 hours and the reaction mixture was then cooled to room temperature. A small amount of insoluble material present was removed by filtration, washed with 3×10 ml portions of acetonitrile and dried (1.1381 gms). Infrared showed this to be BSU plus a small amount of unreacted kanamycin A. The combined filtrate and washings were cooled at 4° for 16 hours. Additional solid separated, was recovered as above, (7.8 gms) and was shown by infrared to be BSU plus urea. The light yellow filtrate and washings were concentrated in vacuo at 40° and dried under high vacuum to give 27.0 gm of a white solid which was partly tacky and partially fine needle-like crystals. The solid was treated with 150 ml of heptane at 23°, the insoluble portion was removed by filtration, washed with 2×50 ml portions of heptane and dried, to give 6.0 gms of white needles (shown by infrared to be BSU plus urea). The combined filtrate and washings were concentrated in vacuo at 40° and dried under high vacuum for 2 hours to give 20.4 gms of white needles, the infrared spectrum of which was typical for polysilylated kanamycin A. Calculations showed the product to contain an average of 7.22 trimethylsilyl groups.

EXAMPLE 15

Preparation of BB-K8 by the Acylation of Per(Trimethylsilyl) Kanamycin A After Partial Desilylation With 1,3-Butanediol A. Preparation of Per(trimethylsilyl) kanamycin A Kanamycin A (10.0 gm, 20.639 m moles) was suspended in 100 ml of sieve-dried acetonitrile, with stirring, at 23°. The suspension was brought to reflux under a nitrogen purge and HMDS (23.322 gms, 144.5 m moles, 7 moles per mole of kanamycin A) was added over a period of ten minutes. Reflux was continued for 16 hours and the mixture was then cooled to room temperature, concentrated in vacuo and dried for 2 hours under high vacuum. There was obtained 24.3 gm of a white, tacky residue (92.1% yield, calculated as kanamycin A (silyl)$_{11}$).

B. Acylation

Per(trimethylsilyl) kanamycin A (24.3 gm) prepared in step A above was dissolved in 240 ml of sieve-dried acetone, with stirring, at 23°. To this solution was added 1,3-butanediol (9.25 ml, 103.2 m mole, 5 moles per mole of per(trimethylsilyl) kanamycin A. The mixture was stirred at 23° for 2 hours under a nitrogen purge and then cooled at 0°-5°. SAE (7.23 gm, 20.64 m moles) in 70 ml of pre-cooled acetone was added over a period of about 1 minute. The mixture was stirred at 0°-5° for 3 hours and then allowed to stand in a 4° cold room for ca. 16 hours. Water (200 ml) was added, the pH was adjusted to 2.5 and the clear yellow solution was stirred at 23° for 30 minutes. The acetone was stripped in vacuo and the aqueous solution was reduced at 55.0 p.s.i. $H_2$ pressure at 23° for 2 hours using 3.0 gm of 10% Pd on carbon as catalyst. The reduced solution was filtered through Dicalite and chromatographed as in Example 11B to give 47.50% BB-K8, 5.87% BB-K29, 7.32% BB-K6, 24.26% kanamycin A and 7.41% polyacyls.

EXAMPLE 16

Preparation of BB-K8 by the Acylation of Poly(trimethylsilyl) Kanamycin A Prepared in THF Using SAE With Sulfamic Acid Catalyst To a refluxing mixture of kanamycin A (5.0 gm, 10.32 m moles) in 50 ml of sieve-dried tetrahydrofuran (THF) were added sulfamic acid (100 mg) and HMDS (12.32 gm, 76.33 m moles). The mixture was refluxed for 18 hours, with complete solution occurring after 6 hours. The solution was cooled to 23°, treated with 0.1 ml of water and held at 23° for 30 minutes. A solution of SAE (3.61 gm, 10.3 m moles) in 36 ml of THF was added over a period of 30 minutes. After stirring for 3 hours, the mixture was diluted with 100 ml of water and the pH was adjusted to 2.2 with 10% $H_2SO_4$. It was stirred for 30 minutes at 23° and then concentrated in vacuo to remove THF. The resulting aqueous solution was reduced at 50 p.s.i. $H_2$ pressure for 2 hours at 23° using 10% Pd on carbon as a catalyst. The reduced solution was filtered through Dicalite and the solids were washed with water. The combined filtrate and washings (150 ml) were determined by microbiological assay against E. coli to contain 1225 mcg/ml (31.5% activity yield) of BB-K8.

EXAMPLE 17

Preparation of BB-K8 by the Acylation of Poly(trimethylsilyl) Kanamycin A with the N-Hyroxysuccinimide Ester of Di-Carbobenzyloxy AHBA

A. Preparation of Dicarbobenzyloxy L-(−)-α-Amino-α-Hydroxybutyric Acid N-Hydroxysuccinimide Ester Dicarbobenzyloxy L-(−)-α-amino-α-hydroxybutyric acid (8 gm, 20.65 m moles) and N-hydroxysuccinimide (2.37 gm, 20.65 m moles) were dissolved in 50 ml of dry acetone at 23°. Dicyclohexylcarbodiimide (4.25 gm, 20.65 m moles) dissolved in 20 ml of dry acetone was added and the total was agitated at 23° for 2 hours. Dicyclohexylurea was filtered off, the filter cake was washed with 10 ml of dry acetone, and the filtrate and washings were combined.

B. Acylation

Poly(trimethylsilyl) kanamycin A, prepared according to the general procedure of Example 15 from 10.0 gms (20.639 m moles) of kanamycin A, was dissolved in 100 ml of dry acetone. The solution was cooled to 0°-5°, 3.7 ml of deionized water was added, and the solution was stirred at 0°-5° for 30 minutes under moderate vacuum.

To this solution was added the solution of the di-Cbz-blocked acylating agent prepared in step A, and the mixture was stirred at 0°-5° for 30 minutes. The mixture was diluted with water, the pH was adjusted to 2.2 and the acetone was removed in vacuo. The aqueous solution was reduced by the general procedure of Example 16 and then filtered through Dicalite. Chromatography showed 40-45% BB-K8, ca. 10% BB-K29, a trace of BB-K6, ca. 30% kanamycin A and a small amount of polyacyls.

EXAMPLE 18

Preparation of Poly(trimethylsilyl) Kanamycin A Using HMDS with Imidazole as Catalyst Kanamycin A (11 gm, 22.7 m moles) and 100 mg of imidazole were heated to reflux in 100 ml of sieve-dried acetonitrile, under a nitrogen purge. HMDS (18.48 gm, 114.5 m moles, 5 moles per mole of kanamycin A) was added over a period of 30 minutes and the mixture was refluxed for 20 hours. Complete solution occurred in ca. 2½ hours. The solution was cooled to 23° and the solvent was removed in vacuo to leave 21.6 gms of poly(trimethylsilyl) kanamycin A as a foamy residue (93.1% yield, calculated as kanamycin(silyl)$_{11}$).

EXAMPLE 19

Preparation of 1-N-[L-(−)-γ-Amino-α-hydroxybutyryl]kanamycin B (BB-K26) by the Acylation of Poly(trimethylsilyl) Kanamycin B With SAE

A. Preparation of Poly(trimethylsilyl) Kanamycin B Using HMDS With TMCS Catalyst Kanamycin B (25 gm, 51.7 m moles) in 250 ml of sieve-dried acetonitrile was heated to reflux under a stream of nitrogen. HMDS (62.3 gm, 385.81 m moles, 7.5 moles per mole of kanamycin B) was added over a period of 30 minutes followed by 1 ml of TMCS as catalyst. The mixture was refluxed for 21 hours with complete solution after 1 hour. The solvent was then removed in vacuo at 60° and the oily residue was held at 60° under high vacuum for 3 hours. There was obtained 53.0 gm of poly(trimethylsilyl) kanamycin B (85.2% yield, calculated as kanamycin B (silyl)$_{10}$).

B. Acylation

The poly(trimethylsilyl) kanamycin B prepared in step A above (53.0 gm) was dissolved in 500 ml of dry acetone at 0°-5°, methanol (20.9 ml) was added, and the mixture was stirred in vacuo for 30 minutes at 0°-5°. A solution of SAE (18.1 gm, 51.67 m moles) in 200 ml of pre-cooled dry acetone was added over a period of less than 1 minute and the mixture was stirred for 30 minutes at 0°-5°. The mixture was worked up according to the general procedure of Example 16 and then loaded on a column of CG-50 (NH$_4$+) (8×120 cm). It was eluted with an NH$_4$OH gradient from 0.6 N to 3 N. There was obtained 38% of BB-K26, 5% of the corresponding 6'-N-acylated kanamycin B (BB-K22), 10% of the corresponding 3-N-acylated kanamycin B (BB-K46) 14.63% kanamycin B and a small amount of polyacylated kanamycin B.

EXAMPLE 20

Preparation of Poly(trimethylsilyl) Kanamycin A Using HMDS With Kanamycin A Sulfate as Catalyst Kanamycin A (19.5 gm, 40.246 m moles) and kanamycin A sulfate (0.5 gm, 0.858 m mole) [total=20.0 gm, 41.0 m moles] in 200 ml of sieve-dried acetonitrile was brought to reflux. HMDS (60.3 ml, 287.7 m moles, 7 moles per mole of kanamycin A) was slowly added and the mixture was refluxed for 28 hours. It was then stripped to dryness on a rotary evaporator and dried under steam injector vacuum. There was obtained 47.5 gms of poly(trimethylsilyl) kanamycin A as a pale yellow oil (95.82% yield, calculated as kanamycin A (silyl)$_{10}$).

EXAMPLE 21

Preparation of BB-K8 by the Acylation of Poly(trimethylsilyl) Kanamycin A With N-Trifluoroacetyl Blocked AHBA N-Hydroxysuccinimide Ester A. Preparation of N-Trifluoroacetyl AHBA and Conversion to its N-Hydroxysuccinimide Ester To a suspension of AHBA (5.0 gm, 42 m moles) in 100 ml THF was added trifluoroacetic anhydride (40 gm, 191 m moles), with stirring, over a 10 minute period. The solution was stirred for 18 hours at 23° and then concentrated to dryness in vacuo at 50°. The residue was dissolved in 100 ml of aqueous methanol (1:1) and stirred for 1 hour. It was then concentrated to dryness in vacuo and redissolved in 50 ml H$_2$O. The aqueous solution was extracted with 3×50 ml portions of MIBK and, after drying over Na$_2$SO$_4$, the extract was concentrated to an oil. Traces of solvent were removed by adding and distilling off 4 ml of water. On standing the oil changed to a waxy, crystalline solid (2.5 gm, 28% yield.

The N-trifluoroacetyl AHBA (2.4 gm, 11.3 m moles) was dissolved in 50 ml dry acetone and N-hydroxysuccinimide (1.30 gm, 11.31 m moles) was added to the solution. A solution of dicyclohexylcarbodiimide (2.33 gm) in 20 ml of dry acetone was slowly added. The reaction mixture was stirred for 2 hours at 23° and the precipitated dicyclohexylurea was removed by filtration and washed with a small amount of acetone. The combined filtrate and washings (a solution of the N-hydroxysuccinimide ester of N-trifluoroacetyl AHBA) was utilized in the next step without isolation.

B. Acylation

To a solution of poly(trimethylsilyl) kanamycin A prepared as in Example 20 (11.31 m moles) in 54 ml of acetone was added 2.0 ml (113.4 m moles) of water, and the mixture was stirred in vacuo at 0°-5° for 30 minutes. The N-hydroxysuccinimide ester of N-trifluoroacetyl AHBA prepared in step A above (11.31 m moles) was added to the mixture and it was then held at 5° for 1 hour. The pH was then adjusted to ca. 2.0 with 20% H$_2$SO$_4$, the mixture was stirred for 30 minutes and the pH was then raised to ca. 6.0 with NH$_4$OH. The mixture was then stripped to dryness in a rotary evaporator to give 14.4 gm of a tacky off-white solid. The solid was dissolved in 100 ml of water, the pH was raised from 5.5 to 11.0 with 10N NH$_4$OH and the solution was heated in an oil bath at 70° for 1 hour. The pH (9.5) was then lowered to 7.0 with HCl, the solution was polish filtered to remove a small amount of insolubles and the filter was washed with water. The combined filtrate and washings (188 ml) was applied to a CG-50 (NH$_4$+) column (8×90 cm), washed with 2 liters of water and eluted with a NH$_4$OH gradient (0.6N-1.0N-concentrated). There was obtained 28.9% BB-K8, 5.0% BB-K6, 5.7% BB-K29, 43.8% kanamycin A, 3.25% polyacyls plus 14.3% of an unknown material which was in the first fraction off the column.

EXAMPLE 22

Preparation of BB-K8 by the Acylation of Poly(trimethylsilyl) Kanamycin A With t-Butyloxycarbonyl Blocked AHBA N-Hydroxysuccinimide Ester A. Preparation of t-BOC AHBA and Conversion to its N-Hydroxysuccinimide Ester A solution of AHBA (5.0 gm, 42 m moles) in 100 ml of water and 20 ml of acetone was adjusted to pH 10 with 10N NaOH. Over a period of 3-4 minutes was added 11.6 gm (53 m moles) of di-t-butyl dicarbonate, and the solution was stirred for 35 minutes while maintaining the pH at 10 by the periodic addition of 10N NaOH. The acetone was removed in vacuo and the aqueous phase was washed with 40 ml of ethyl acetate. The pH of the aqueous solution was lowered to 2.0 with 3N HCl and it was then extracted with 3×30 ml of MIBK. The combined MIBK extracts were dried over Na$_2$SO$_4$ and concentrated to a clear oily residue (8.2 gm, 89%).

The t-BOC-AHBA (4.25 gm, 19.4 m moles) was dissolved in 50 ml of acetone and N-hydroxysuccinimide (2.23 gm, 19.4 m moles) was added. A solution of dicyclohexylcarbodiimide (4.00 gm 19.4 m moles) in 20 ml of acetone was slowly added and the mixture was stirred for 2 hours at 23°. The precipitated dicyclohexylurea was removed by filtration and was washed with a small amount of acetone. The combined filtrate and washings (a solution of the N-hydroxysuccinimide ester of t-BOC-AHBA) was utilized in the next step without isolation.

B. Acylation

To a solution of poly(trimethylsilyl) kanamycin A prepared as in Example 20 (41.28 m moles) in 94 ml of acetone was added 3.5 ml (194 m moles) of water, and the mixture was stirred in vacuo at 0°-5° for 30 minutes. The N-hydroxysuccinimide ester of t-BOC-AHBA prepared in step A above (19.4 m moles) was added and the mixture was allowed to stand at 5° for 1 hour. Water (200 ml) was added and the pH (7.0) was lowered to 2.0 with 20% H$_2$SO$_4$. After 30 minutes stirring the pH was raised to ca. 6.0 with NH$_4$OH and the mixture was stripped to dryness in vacuo to give 36.3 gms of a golden oil. The oil was dissolved in 200 ml of trifluoroacetic acid, allowed to stand for 15 minutes and stripped to dryness in a rotary evaporator. The oil was washed with water and the water was flashed off. Concentrated NH$_4$OH was added to pH 6.0 and was flashed off. The resulting solid was dissolved in water, filtered, and the filter washed with water. The combined filtrate and washings (259 ml) were loaded on a CG-50 (NH$_4$+) column (8×92 cm), washed with 4 liters of water and eluted with an NH$_4$OH gradient (0.6 N-1.0 N-concentrated). There was obtained 40.32% BB-K8, 4.58% BB-K6, 8.32% BB-K29, 30.50% kanamycin A and 7.43%. polyacyls.

EXAMPLE 23

The general procedure of Example 10 is repeated except that the kanamycin A utilized therein is replaced by an equimolar amount of
3'-deoxykanamycin A,
6'-N-methylkanamycin A,
3'-deoxy-6'-N-methylkanamycin A,
Kanamycin B,
6'-N-methylkanamycin B,
tobramycin (3'-deoxykanamycin B),
6'-N-methyltobramycin,
aminoglycoside NK-1001,
3'-deoxy aminoglycoside NK-1001,
6'-N-methyl aminoglycoside NK-1001,
3'-deoxy-6'-N-methyl aminoglycoside NK-1001,
gentamicin A,
3'-deoxygentamicin A,
gentamicin B,
3'-deoxygentamicin B,
6'-N-methylgentamicin B,
3'-deoxy-6'-N-methylgentamicin B,
gentamicin $B_1$,
3'-deoxygentamicin $B_1$,
6'-methylgentamicin $B_1$,
3'-deoxy-6'-N-methylgentamicin $B_1$,
gentamicin $X_2$,
seldomycin factor 1 and seldomycin factor 2, respectively,
and there is thereby produced
1-N-[L-(−)-γ-amino-α-hydroxybutyryl]-3'-deoxykanamycin A,
1-N-[L-(−)-γ-amino-α-hydroxybutyryl]-6'-N-methylkanamycin A,
1-N-[L-(−)-γ-amino-α-hydroxybutyryl]-3'-deoxy-6'-N-methyl-kanamycin A
1-N-[L-(−)-γ-amino-α-hydroxybutyryl]kanamycin B,
1-N-[L-(−)-γ-amino-α-hydroxybutyryl]-6'-N-methylkanamycin B,
1-N-[L-(−)-γ-amino-α-hydroxybutyryl]tobramycin
1-N-[L-(−)-γ-amino-α-hydroxybutyryl]-6'-N-methyltobramycin,
1-N-[L-(−)-γ-amino-α-hydroxybutyryl]aminoglycoside NK-1001,
1-N-[L-(−)-γ-amono-α-hydroxybutyryl]-3'-deoxy aminoglycoside NK-1001,
1-N-[L-(−)-γ-amino-α-hydroxybutyryl]-6'-N-methyl aminoglycoside NK-1001,
1-N-[L-(−)-γ-amino-α-hydroxybutyryl]-3'-deoxy-6'-N-methyl aminoglycoside NK-1001,
1-N-[L-(−)-γ-amino-α-hydroxybutyryl]gentamicin A,
1-N-[L-(−)-γ-amino-α-hydroxybutyryl]-3'-deoxygentamicin A,
1-N-[L-(−)-γ-amino-α-hydroxybutyryl]gentamicin B,
1-N-[L-(−)-γ-amino-α-hydroxybutyryl]-3'-deoxygentamicin B,
1-N-[L-(−)-γ-amino-α-hydroxybutyryl]-6'-N-methylgentamicin B,
1-N-[L-(−)-γ-amino-α-hydroxybutyryl]-3'-deoxy-6'-N-methylgentamicin $B_1$,
1-N-[L-(−)-γ-amino-α-hydroxybutyryl]gentamicin $B_1$,
1-N-[L-(−)-γ-amino-α-hydroxybutyryl]-3'-deoxygentamicin $B_1$,
1-N-[L-(−)-γ-amino-α-hydroxybutyryl]-6'-N-methylgentamicin $B_1$,
1-N-[L-(−)-γ-amino-α-hydroxybutyryl]-3'-deoxy-6'-N-methylgentamicin $B_1$,
1-N-[L-(−)-γ-amino-α-hydroxybutyryl]gentamicin $X_2$,
1-N-[L-(−)-γ-amino-α-hydroxybutyryl] seldomycin factor 1 and
1-N-[L-(−)-γ-amino-α-hydroxybutyryl] seldomycin factor 2, respectively.

The reaction of each of the aminoglycoside starting materials listed above in the same manner with L-(−)-β-benzyloxycarbonylamino-α-hydroxypropionic acid N-hydroxy-5-norbornene-2,3-dicarboximide ester instead of the L-(−)-γ-benzyloxycarbonylamino-α-hydroxybutyric acid N-hydroxy-5-norbornene-2,3-dicarboximide ester produces the corresponding 1-N-[L-(−)-β-amino-α-hydroxypropionyl] aminoglycosides.

The reaction of each of the aminoglycoside starting materials listed above in the same manner with L-(−)-δ-benzyloxycarbonylamino-α-hydroxyvaleric acid N-hydroxy-5-norbornene-2,3-dicarboximide ester instead of the L-(−)-γ-benzyloxycarbonylamino-α-hydroxybutyric acid N-hydroxy-5-norbornene-2,3-dicarboximide ester produces the corresponding 1-N-[L-(−)-δ-amino-α-hydroxyvaleryl] aminoglycosides.

EXAMPLE 24

The general procedure of Example 10 is repeated except that the L-(−)-γ-benzyloxycarbonylamino-α-hydroxybutyric acid N-hydroxy-5-norbornene-2,3-dicarboximide ester used therein is replaced by
L-(−)-β-benzyloxycarbonylamino-α-hydroxypropionic acid N-hydroxy-5-norbornene-2,3-dicarboximide ester and
L-(−)-δ-benzyloxycarbonylamino-α-hydroxyvaleric acid N-hydroxy-5-norbornene-2,3-dicarboximide ester, respectively,
and there is thereby produced
1-N-[L-(−)-β-amino-α-hydroxypropionyl]kanamycin A and
1-N-[L-(−)-δ-amino-α-hydroxyvaleryl]kanamycin A, respectively.

EXAMPLE 25

The general procedure of Example 1 is repeated, except that the 6'-N-carbobenzyloxykanamycin A utilized therein is replaced by an equimolar amount of
6'-carbobenzyloxy-3',4'-dideoxykanamycin A,
6'-carbobenzyloxy-3',4'-dideoxy-6'-N-methylkanamycin A,
2',6'-di-(N-carbobenzyloxy)-3',4'-dideoxykanamycin B,
2',6'-di-(N-carbobenzyloxy)-3',4'-dideoxy-6'-N-methylkanamycin B,
2',6'-di-(N-carbobenzyloxy)gentamicin $C_1$,
2',6'-di-(N-carbobenzyloxy)gentamicin $C_{1a}$,
2',6'-di-(N-carbobenzyloxy)-6'-N-methylgentamicin $C_{1a}$,
2',6'-di-(N-carbobenzyloxy)gentamicin $C_2$,
2',6'-di-(N-carbobenzyloxy)-6'-N-methylgentamicin $C_2$ and
2',6'-di-(N-carbobenzyloxy)aminoglycoside XK-62-2, respectively,
and there is thereby produced
1-N-[L-(−)-γ-amino-α-hydroxybutyryl]-3',4'-dideoxykanamycin A,
1-N-[L-(−)-γ-amino-α-hydroxybutyryl]-3',4'-dideoxy-6'-N-methylkanamycin A,
1-N-[L-(−)-γ-amino-α-hydroxybutyryl]-3',4'-dideoxykanamycin B, 1-N-[L-(—)-γ-amino-α-hydroxybutyryl]-3',4'-dideoxy-6'-N-methylkanamycin B,
1-N-[L-(—)-γ-amino-α-hydroxybutyryl]gentamicin C$_1$,
1-N-[L-(—)-γ-amino-α-hydroxybutyryl]gentamicin C$_{1a}$,
1-N-[L-(—)-γ-amino-α-hydroxybutyryl]-6'-N-methylgentamicin C$_{1a}$,
1-N-[L-(—)-γ-amino-α-hydroxybutyryl]gentamicin C$_2$,
1-N-[L-(—)-γ-amino-α-hydroxybutyryl]-6'-N-methylgentamicin C$_2$ and
1-N-[L-(—)-γ-amino-α-hydroxybutyryl] aminoglycoside XK-62-2, respectively.

The reaction of each of the aminoglycoside starting materials listed above in the same manner with L-(—)-β-benzyloxycarbonylamino-α-hydroxypropionic acid N-hydroxy-5-norbornene-2,3-dicarboximide ester instead of the L-(—)-γ-benzyloxycarbonylamino-α-hydroxybutyric acid N-hydroxy-5-norbornene-2,3-dicarboximide ester produces the corresponding 1-N-[L-(—)-β-amino-α-hydroxypropionyl] aminoglycosides.

The reaction of each of the aminoglycoside starting materials listed above in the same manner with L-(—)-δ-benzyloxycarbonylamino-α-hydroxyvaleric acid N-hydroxy-5-norbornene-2,3-dicarboximide ester instead of the L-(—)-γ-benzyloxycarbonylamino-α-hydroxybutyric acid N-hydroxy-5-norbornene-2,3-dicarboximide ester produces the corresponding 1-N-[1-(—)-δ-amino-α-hydroxyvaleryl] aminoglycosides.

EXAMPLE 26

2',6'-di-(N-Trifluoroacetyl)sisomicin is slurried in dry acetonitrile and heated to reflux under a nitrogen atmosphere. Hexamethyldisilazane [4 moles per mole of 2'6'-di-(N-trifluoroacetyl)sisomicin] is added over a period of 30 minutes and the resulting solution is refluxed for 24 hours. Removal of the solvent in vacuo gives solid polysilylated 2',6'-di-(N-trifluoroacetyl)sisomicin.

The polysilylated 2',6'-di-(N-trifluoroacetyl)sisomicin is acylated with the N-hydroxysuccinimide ester of L-(—)-γ-trifluoroacetylamino-α-hydroxybutyric acid according to the general procedure of Example 21B and worked up as in Example 21B to give 1-N-[L-(—)-γ-amino-γ-hydroxybutyryl]sisomicin.

EXAMPLE 27

The general procedure of Example 26 is repeated except that the 2',6'-di-(N-trifluoroacetyl)sisomicin utilized therein is replaced by an equimolar amount of
2',6'-di-(N-trifluoroacetyl)-5-episisomicin,
2',6'-di-(N-trifluoroacetyl)-6'-N-methylsisomicin,
2',6'-di-(N-trifluoroacetyl)-6'-N-methyl-5-episisomicin,
2',6'-di-(N-trifluoroacetyl)verdamicin,
2',6'-di-(N-trifluroracetyl)-5-epiverdamicin,
2',6'-di-(N-trifluoroacetyl)-6'-N-methylverdamicin,
2',6'-di-(N-trifluoroacetyl)-6'-N-methyl-5-epiverdamicin and
2',6'-di-(N-trifluoroacetyl) aminoglycoside 66-40D, respectively,
and there is thereby produced
1-N-[L-(—)-γ-amino-α-hydroxybutyryl]-5-episisomicin,
1-N-[L-(—)-γ-amino-α-hydroxybutyryl]-6'-methylsisomicin,
1-N-[L-(—)-γ-amino-α-hydroxybutyryl]-6'-N-methyl-5-episisomicin,
1-N-[L-(—)-γ-amino-α-hydroxybutyryl]verdamicin,
1-N-[L-(—)-γ-amino-α-hydroxybutyryl]-5-epiverdamicin,
1-N-[L-(—)-γ-amino-α-hydroxybutyryl]-6'-N-methylverdamicin,
1-N-[L-(—)-γ-amino-α-hydroxybutyryl]-6'-N-methyl-5-epiverdamicin and
1-N-[L-(—)-γ-amino-α-hydroxybutyryl] aminoglycoside 66-40D, respectively.

The reaction of each of the 2',6'-di-(N-trifluoroacetyl) aminoglycoside starting materials listed above in the same manner with the N-hydroxysuccinimide ester of L-(—)-β-trifluoroacetylamino-α-hydroxypropionic acid instead of the N-hydroxysuccinimide ester of L-(—)-γ-trifluoroacetylamino-α-hydroxybutyric acid produces the corresponding 1-N-[L-(—)-β-amino-α-hydroxypropionyl] aminoglycosides.

The reaction of each of the 2',6'-di-(N-trifluoroacetyl) aminoglycoside starting materials listed above in the same manner with the N-hydroxysuccinimide ester of L-(—)-δ-trifluoroacetylamino-α-hydroxyvaleric acid instead of the N-hydroxysuccinimide ester of L-(—)-γ-trifluoroacetylamino-α-hydroxybutyric acid produces the corresponding 1-N-[L-(—)-δ-amino-α-hydroxyvaleryl] aminoglycosides.

EXAMPLE 28

The general procedure of Example 26 is repeated except that the N-hydroxysuccinimide ester of L-(—)-γ-trifluoroacetylamino-α-hydroxybutyric acid is replaced by an equimolar amount of the N-hydroxysuccinimide esters of
L-(—)-β-trifluoroacetylamino-α-hydroxypropionic acid and
L-(—)-δ-trifluoroacetylamino-α-hydroxyvaleric acid, respectively,
and there is thereby produced
1-N-[L-(—)-β-amino-α-hydroxypropionyl]sisomicin and
1-N-[L-(—)-δ-amino-α-hydroxyvaleryl]sisomicin, respectively.

EXAMPLE 29

The general procedure of Example 1 is repeated except that the 6'-N-carbobenzyloxykanamycin A utilized therein is replaced by an equimolar amount of
3-N-carbobenzyloxyribostamycin,
3-N-carbobenzyloxy-3'-deoxyribostamycin,
3-N-carbobenzyloxy-6'-N-methylribostamycin,
3-N-carbobenzyloxy-6'-N-methyl-3'-deoxyribostamycin,
3-N-carbobenzyloxyneomycin B,
3-N-carbobenzyloxy-3'-deoxyneomycin B,
3-N-carbobenzyloxy-6'-N-methylneomycin B,
3-N-carbobenzyloxy-6'-N-methyl-3'-deoxyneomycin B,
3-N-carbobenzyloxyneomycin C,
3-N-carbobenzyloxy-3'-deoxyneomycin C,
3-N-carbobenzyloxy-6'-N-methylneomycin C,
3-N-carbobenzyloxy-6'-N-methyl-3'-deoxyneomycin C,
3-N-carbobenzyloxyxylostasin,
3-N-carbobenzyloxy-3'-deoxyxylostasin,
3-N-carbobenzyloxy-6'-N-methylxylostasin,
3-N-carbobenzyloxy-6'-N-methyl-3'-deoxyxylostasin,
3-N-carbobenzyloxyparomomycin I,
3-N-carbobenzyloxy-3'-deoxyparomomycin I,
2',3-di-(N-carbobenzyloxy)-3',4'-dideoxyparomomycin I,
3-N-carbobenzyloxyparomomycin II,
3-N-carbobenzyloxy-3'-deoxyparomomycin II, 2',3-di-(N-carbobenzyloxy)-3',4'-dideoxyparomomycin II,
3-N-carbobenzyloxy aminoglycoside 2230-C,
3-N-carbobenzyloxy-3'-deoxy aminoglycoside 2230-C,
3-N-carbobenzyloxylividomycin A and
3-N-carbobenzyloxylividomycin B, respectively,
and there is thereby produced
1-N-[1-(—)-γ-amino-α-hydroxybutyryl]ribostamycin,
1-N-[L-(—)-γ-amino-α-hydroxybutyryl]-3'-deoxyribostamycin,
1-N-[L-(—)-γ-amino-α-hydroxybutyryl]-6'-N-methylribostamycin,
1-N-[L-(—)-γ-amino-α-hydroxybutyryl]-6'-N-methyl-3'-deoxyribostamycin,
1-N-[L-(—)-γ-amino-α-hydroxybutyryl]neomycin B,
1-N-[L-(—)-γ-amino-α-hydroxybutyryl]3'-deoxyneomycin B,
1-N-[L-(—)-γ-amino-α-hydroxybutyryl]-6'-N-methylneomycin B,
1-N-[L-(—)-γ-amino-α-hydroxybutyryl]-6'-N-methyl-3'-deoxyneomycin B,
1-N-[L-(—)-γ-amino-α-hydroxybutyryl]neomycin C,
1-N-[L-(—)-γ-amino-α-hydroxybutyryl]-3'-deoxyneomycin C,
1-N-[L-(—)-γ-amino-α-hydroxybutyryl]-6'-N-methylneomycin C
1-N-[L-(—)-γ-amino-α-hydroxybutyryl]-6'-N-methyl-3'-deoxyneomycin C,
1-N-[L-(—)-γ-amino-α-hydroxybutyryl]xylostasin,
1-N-[L-(—)-γ-amino-α-hydroxybutyryl]-3'-deoxyxylostasin,
1-N-[L-(—)-γ-amino-α-hydroxybutyryl]-6'-N-methylxylostasin,
1-N-[L-(—)-γ-amino-α-hydroxybutyryl]-6'-N-methyl-3'-deoxyxylostasin,
1-N-[L-(—)-γ-amino-α-hydroxybutyryl]paromomycin I,
1-N-[L-(—)-γ-amino-α-hydroxybutyryl]-3'-deoxyparomomycin I,
1-N-[L-(—)-γ-amino-α-hydroxybutyryl]-3',4'-dideoxyparomomycin I,
1-N-[L-(—)-γ-amino-α-hydroxybutyryl]paromomycin II,
1-N-[L-(—)-γ-amino-α-hydroxybutyryl]-3'-deoxyparomomycin II,
1-N-[L-(—)-γ-amino-α-hydroxybutyryl]-3',4'-dideoxyparomomycin II,
1-N-[L-(—)-γ-amino-α-hydroxybutyryl]aminoglycoside 2230-C,
1-N-[L-(—)-γ-amino-α-hydroxybutyryl]-3'-deoxy aminoglycoside 2230-C,
1-N-[L-(—)-γ-amino-α-hydroxybutyryl]lividomycin A and
1-N-[L-(—)-γ-amino-α-hydroxybutyryl]lividomycin B, respectively.

The reaction of each of the carbobenzyloxy-protected aminoglycoside starting materials listed above in the same manner with L-(—)-β-benzyloxycarbonylamino-α-hydroxypropionic acid N-hydroxy-5-norbornene-2,3-dicarboximide ester instead of the L-(—)-γ-benzyloxycarbonylamino-α-hydroxybutyric acid N-hydroxy-5-norbornene-2,3-dicarboximide ester produces the corresponding 1-N-[L-(—)-β-amino-α-hydroxypropionyl] aminoglycosides.

The reaction of each of the carbobenzyloxy-protected aminoglycoside starting materials listed above in the same manner with L-(—)-δ-benzyloxycarbonylamino-α-hydroxyvaleric acid N-hydroxy-5-nor-bornene-2,3-dicarboximide ester instead of the L-(—)-γ-benzyloxycarbonylamino-α-hydroxybutyric acid N-hydroxy-5-norbornene-2,3-dicarboximide ester produces the corresponding 1-N-[L-(—)-δ-amino-α-hydroxyvaleryl] aminoglycosides.

EXAMPLE 30

The general procedure of Example 1 is repeated except that the 6'-N-carbobenzyloxykanamycin A utilized therein is replaced by an equimolar amount of
2',3,6'-tri-(N-carbobenzyloxy)-3',4'-dideoxyribostamycin,
2',3,6'-tri-(N-carbobenzyloxy)-3',4'-dideoxyneomycin B,
2',3,6'-tri-(N-carbobenzyloxy)-3',4'-dideoxyneomycin C and
2',3,6'-tri-(N-carbobenzyloxy)-3',4'-dideoxylostasin, respective,
and there is thereby produced
1-N-[L-(—)-γ-amino-α-hydroxybutyryl]-3',4-dideoxyribostamycin,
1-N-[L-(—)-γ-amino-α-hydroxybutyryl]-3',4'-dideoxyneomycin B,
1-N-[L-(—)-γ-amino-α-hydroxybutyryl]-3',4'-dideoxyneomycin C and
1-N-[L-(—)-γ-amino-α-hydroxybutyryl]-3',4'-dideoxyxylostasin, respectively.

The reaction of each of the 2',3,6'-tri-(N-carbobenzyloxy)protected aminoglycoside starting materials listed above in the same manner with L-(—)-β-benzyloxycarbonylamino-α-hydroxypropionic acid N-hydroxy-5-norbornene-2,3-dicaboximide ester instead of the L-(—)-γ-benzyloxycarbonylamino-α-hydroxybutyric acid N-hydroxy-5-norbornene-2,3-dicarboximide ester produces the corresponding 1-N-[L-(—)-β-amino-α-hydroxypropionyl]aminoglycosides.

The reaction of each of the 2',3,6'-tri-(N-carbobenzyloxy)protected aminoglycoside starting materials listed above in the same manner with L-(—)-δ-benzyloxycarbonylamino-α-hydroxy acid N-hydroxy-5-norbornene-2,3-dicarboximide ester instead of the L-(—)-γ-benzyloxycarbonylamino-α-hydroxybutyric acid N-hydroxy-5-norbornene-2,3-dicarboximide ester produces the corresponding 1-N-[L-(—)-δ-amino-α-hydroxy] aminoglycosides.

EXAMPLE 31

Preparation of 1-N-[L-(—)-γ-Amino-α-hydroxybutyryl]-4'-deoxy-6'-N-methylkanamycin A (BB-K311) by Acylation of Polysilylated 6'-N-Benzyl-3-N-carbobenzyloxy-4'-deoxy-6'-N-methylkanamycin A A. 6'-N-Carbobenzyloxy-4'-deoxykanamycin A and 3,6'-di-N-carbobenzyloxy-4'-deoxykanamycin A To a stirred solution of 10.4 g (22.2 m mol) of 4'-deoxykanamycin A and 27.5 g (111 m mol) of Ni(OAc)$_2$.4-H$_2$O in 450 ml of DMSO was added 7.0 g (22.4 m mol) of the N-hydroxy-5-norbornene-2,3-dicarboximide ester of benzyloxyformic acid (Cbz-ONB) at ca 10° C. and stirred overnight at room temperature. The reaction mixture was concentrated in vacuo to give a blue, oily residue, which was chromatographed over CG-50 resin (NH$_4$+, 500 ml), eluting with dilute ammonia-water. The ninhydrin positive fractions, collected from the waste (due to a leak of the 3,6'-di-N-Cbz derivative) and the elute with 0.1 N ammonia, were combined and evaporated in vacuo. The residue was rechromatographed over Diaion HP-10 resin (400 ml) using aqueous methanol as an eluant to separate the mono- and di-Cbz derivatives. The 6'-N-Cbz derivative, eluted with 30% aqueous methanol, was crystallized from $H_2O$-ethanol to give 4.73 g (35%) of colorless crystals. Mp 232°–233° C. IR(KBr): 1700, 1540, 1275, 1135, 1075, 1040, 770, 750, 695 cm$^{-1}$.

Anal. Calcd. for $C_{26}H_{42}N_4O_{12}\cdot EtOH\cdot\frac{1}{2}H_2O$: C, 51.13; H, 7.51; N, 8.52. Found: C, 51.03, H, 7.31; N, 8.42.

The 3,6'-di-N-Cbz derivative, eluted with 90% aqueous methanol, was crystallized from $H_2O$-methanol to give 3.08 g (18.4%) of needles, mp 220°–221° C., IR(KBr): 1690, 1545, 1260, 1135, 1075, 1045, 780, 750, 700 cm$^{-1}$.

Anal. Calcd. for $C_{34}H_{48}N_4O_{14}\cdot H_2O$: C, 54.10; H, 6.68; N, 7.42. Found: C, 54.10; H, 6.69; N, 7.07.

B. 1,3,3''-Tri-N-acetyl-6'-N-carbobenzyloxy-4'-deoxykanamycin A

To a stirred suspension of 4.70 g (7.8 m mol) of 3,6'-di-N-Cbz-4'-deoxykanamycin A in 240 ml methanol was added 29 ml (307 m mol) of acetic anhydride. The mixture was stirred overnight at room temperature, and evaporated in vacuo to afford 5.68 g (100%) of the title tri-N-acetyl derivative, mp 290°–291° C. (dec.), IR(KBr): 1700, 1650, 1550, 1380, 1260, 1140, 1080, 1035, 745, 695 cm$^{-1}$.

Anal. Calcd. for $C_{32}H_{48}N_4O_{15}\cdot H_2O$: C, 51.47; H, 6.75; N, 7.50. Found: C, 51.66; H, 7.13; N, 7.06.

C. 1,3,3''-Tri-N-acetyl-4'-deoxykanamycin A

A solution of 5.5 g (7.6 m mol) of 1,3,3''-tri-N-acetyl-6'-N-carbobenzyloxy-4'-deoxykanamycin A in 80 ml of 50% aqueous ethanol was hydrogenated for 18 hours with 1 g of 10% Pd-C at atmospheric pressure and room temperature. The catalyst was removed by filtration and the filtrate was evaporated under reduced pressure to give 4.49 g (100%) of the title compound. An analytical sample was prepared by column chromatography on Amberlite IRA-410 resin (OH$^-$) and crystallization from $H_2O$-methanol, mp 280°–283° C., (IR(KBr): 1650, 1550, 1380, 1135, 1080, 1035 cm$^{-1}$.

Anal. calcd. for $C_{24}H_{42}N_4O_{13}\cdot MeOH\cdot\frac{1}{2}H_2O$: C, 47.24; H, 7.45; N, 8.81. Found: C, 47.61; H, 7.45; N, 8.58.

D. 1,3,3''-Tri-N-acetyl-6'-N-benzyl-4'-deoxykanamycin A

A solution of 4.39 g (7.39 m mol) of 1,3,3''-tri-N-acetyl-4'-deoxykanamycin A and 5 ml of benzaldehyde in 60 ml of aqueous methanol was heated at 60° C. for 30 minutes. The reaction mixture was cooled, treated with 4.0 g (106 m mol) of $NaBH_4$, stirred for 2 days at room temperature and evaporated in vacuo. The oily residue was chromatographed over HP-10 resin (150 ml) using aqueous methanol as an eluant to afford 3.86 g (74%) of the title compound and 1.70 g of moist starting material, which was recycled in the same process giving an additional 1.32 g (26%) of the title compound. An analytical sample was prepared by re-chromatography on HP-10 resin and crystallization from $H_2O$-ethanol, mp >300° C., IR(KBr): 3280, 1640, 1555, 1380, 1135, 1080, 1040, 750, 700 cm$^{-1}$.

Anal. Calcd. for $C_{31}H_{48}N_4O_{13}$: C, 54.38; H, 7.07; N, 8.18. Found: C, 54.01; H, 7.16; N, 7.87.

E. 1,3,3''-Tri-N-acetyl-6'-N-benzyl-4'-deoxy-6'-N-methylkanamycin A

To a stirred mixture of 3.86 g (5.6 m mol) of 1,3,3''-tri-N-acetyl-6'-N-benzyl-4'-deoxykanamycin A and 5.6 ml of 37% aqueous HCHO in 85 ml of 95% methanol was added 850 mg (13.5 m mol) of $NaBH_3CN$. The mixture was stirred for 4 hours at room temperature and evaporated to dryness. The residue was chromatographed over HP-10 resin using aqueous methanol as an eluant to afford 3.88 g (100%) of the title compound. An analytical sample was obtained by crystallization from $H_2O$-ethanol, mp 295°–297° C. (dec.). IR(KBr): 3280, 1645, 1500, 1375, 1145, 1075, 1040, 740, 700 cm$^{-1}$. NMR($D_2O$): δ in ppm from DSS, 2.27 (3H, s, N-CH$_3$), 7.34 (5H, s, Ar-H). Anal. Calcd. for $C_{32}H_{50}N_4O_{13}\cdot\frac{1}{2}H_2O$: C, 54.30; H, 7.26; N, 7.92. Found: C, 54.30; H, 7.33; N, 7.64.

F. 6'-N-Benzyl-4'-deoxy-6'-N-methylkanamycin A (BB-K312)

A mixture of 5.18 g (7.42 m mol) of 1,3,3''-tri-N-acetyl-6'-N-benzyl-4'-deoxy-6'-N-methylkanamycin A and 15 g of NaOH in 80 ml of $H_2O$ was refluxed overnight. The mixture was cooled, neutralized with concentrated HCl and filtered to remove the insoluble materials. The filtrate was introduced on the top of a column of CG-50 resin ($NH_4^+$, 370 ml). After washing with 1.5 L of water, the column was eluted successively with 2 L of 0.05 N $NH_4OH$ and 2 L of 0.1 N $NH_4OH$. The eluate which showed positive ninhydrin reaction was evaporated to give 3.23 g (76%) of the title compound.

G. 6'-N-Benzyl-3-N-benzyloxycarbonyl-4'-deoxy-6'-N-methylkanamycin A

To a stirred solution of 2.94 g (5.14 m mol) of 6'-N-benzyl-4'-deoxy-6'-N-methylkanamycin A (BB-K312) and 6.37 g (25.7 m mol) of $Ni(OAc)_2\cdot 4H_2O$ in 100 ml of DMSO was added 1.62 g (5.20 m mol) of Cbz-ONB and stirring was continued at room temperature. After 2 days, 72 ml of 0.2 M aqueous EDTA solution and 30 ml of concentrated $NH_4OH$ was added to the reaction mixture. The resulting blue solution was introduced on the top of a column of HP-10 resin (150 ml). After washing with 200 ml of 7 N $NH_4OH$ and then with 300 ml of $H_2O$, the column was eluted with 400 ml of 80% aqueous methanol to give 2.65 g (73%) of the title compound. An analytical sample was prepared by crystallization from methanol, mp 216°–217° C. IR(KBr): 3340, 1690, 1540, 1290, 1135, 1045, 745, 700 cm$^{-1}$.

Anal. Calcd. for $C_{34}H_{50}N_4O_{12}\cdot\frac{1}{2}H_2O$: C, 57.06; H, 7.18; N, 7.83. Found: C, 57.29; H, 7.22; N, 7.58.

H. 1-N-[L-(−)-γ-Amino-α-hydroxybutyryl]-4'-deoxy-6'-N-methylkanamycin A (BB-K311)

A suspension of 2.49 g (3.53 m mol) of 6'-N-benzyl-3-N-benzyloxycarbonyl-4'-deoxy-6'-N-methylkanamycin A and 5 ml of HMDS in 40 ml of dry $CH_3CN$ was refluxed overnight. The resulting clear solution was concentrated to dryness. To a stirred solution of the oily residue in 50 ml diethyl ketone was added 1.23 g (3.51 m mol) of SAE. The mixture was stirred overnight at room temperature and evaporated in vacuo to afford an oily residue, which was treated with $H_2O$-ethanol, adjusted to pH ca 3 with 1 N HCl and allowed to stand for 30 minutes at room temperature. This solution, containing the acylated product (a small sample isolated from the solution showed a carbonyl absorption at 1655 cm$^{-1}$ owing to an amide), was hydrogenated overnight with 1 g of 10% Pd-C at atmospheric pressure and room temperature. The catalyst was removed by filtration and the filtrate was evaporated in vacuo. The residue was dissolved in a small amount of water and the solution was introduced into the top of a column of CG-50 resin (NH$_4^+$, 160 ml). After washing with 250 ml of water, the column was eluted successively with 250 ml of 0.1 N NH$_4$OH, 1 L of 0.2 N NH$_4$OH and finally 1 L of 0.5 N NH$_4$OH. The eluate was collected in 20-ml fractions. Fractions 89–100 which showed positive ninhydrin reaction were evaporated in vacuo to give an oily residue. The residue solidified in H$_2$O-ethanol to give 1.255 g of crystalline product and 144 mg of a second crop, total 1.399 g (68%) of the title product, mp 182°–184° C., $[\alpha]_D^{22°} +93°$ (c 1, H$_2$O).

Anal. Calcd. for C$_{23}$H$_{45}$N$_5$O$_{12}$.EtOH.H$_2$O: C, 46.36; H, 8.25; N, 10.81. Found: C, 46.37; H, 8.40; N, 10.38.

This product was rechromatographed over CG-50 resin (NH$_4^+$, 100 ml) using carbonate free aqueous ammonia as an eluant and crystallized from H$_2$O-methanol-isopropanol to give 927 mg of the title compound as colorless needles, mp 193°–194° C., $[\alpha]_D^{22°} +101°$ (c 1, H$_2$O). NMR(D$_2$O): δ in ppm from DSS, 1.37 (2H, q, J=12,2-Hax & 4-Hax), 1.86 (4H, m, 2-Heq, 4'-Heq & β-CH$_2$), 2.29 (3H, s, N-CH$_3$), 4.14 (1H, dd, J=8 & 4.5,α-CH), 5.00 (1H,d,J=3.5,1''-H), 5.24 (1H,d,J=3.5,1'-H). IR(KBr): 1640, 1540, 1135, 1080, 1040, 955 cm$^{-1}$.

Anal. Calcd. for C$_{23}$H$_{45}$N$_5$O$_{12}$.2H$_2$O: C, 44.58; H, 7.97; N, 11.30. Found: C, 44.85; H, 7.90; N, 11.85.

EXAMPLE 32

Preparation of
1-N-[L-(−)-γ-Amino-α-hydroxybutyryl]-4'-deoxykanamycin A (BB-K160) by Acylation of Polysilylated
3,6'-di-N-Carbobenzyloxy-4'-deoxykanamycin A A suspension of 2.27 g (3.08 m mol) of 3,6'-di-N-carbobenzyloxy-4'-deoxykanamycin A and 5 ml of HMDS in 35 ml of dry CH$_3$CN was refluxed 2 days. The resulting clear solution was concentrated in vacuo. The oily residue was dissolved in 40 ml of dry diethyl ketone. To the solution was added 1.08 g (3.08 m mol) of SAE with stirring. The mixture was stirred overnight at room temperature and evaporated to dryness. The residue was treated with ethanol-H$_2$O and adjusted to pH 3 with 1 N HCl. After standing for 30 minutes, the acidic solution was hydrogenated for 3 days with 1.2 g of 10% Pd-C at atmospheric pressure and room temperature. The catalyst was removed by filtration and the filtrate was evaporated in vacuo. The residue was dissolved in a small amount of water and the solution was introduced into the top of a CG-50 resin (NH$_4^+$, 130 ml) column. After washing with 500 ml of H$_2$O, the column was eluted successively with 1 L of 0.2 N NH$_4$OH and 1 L of 0.5 N NH$_4$OH. The eluate was collected in 20-ml fractions. Fractions 79–95 which showed positive ninhydrin test were combined and evaporated in vacuo to give 1 g (56.1%) of the title compound as an amorphous powder. The product was crystallized by the same procedure used for BB-K311 in Step H of Example 31, mp 179°–180° C., $[\alpha]_D^{20°} +99°$ (c 1, H$_2$O). IR(KBr): 1640, 1535, 1120, 1065, 1030, 945 cm$^{-1}$. NMR(D$_2$O): δ in ppm, 1.37 (2H,q,J=12,2- & 4'-Hax), 1.86 (4H, m,2- &

4'-Heq & β-CH$_2$), 4.13 (1H,dd,J=8 & 4.5,α-CH), 5.02 (1H,d,J=3,1''-H), 5.28 (1H,d,J=3.5,1'-H).

Anal. Calcd. for C$_{22}$H$_{43}$N$_5$O$_{12}$.½MeOH.2H$_2$O: C, 43.47; H, 7.95; N, 11.27. Found: C, 43.69; H, 7.92; N, 10.91.

We claim:

1. A process for the preparation of a 1-N-[ω-amino-α-hydroxyalkanoyl]aminoglycoside antibiotic of the formula I

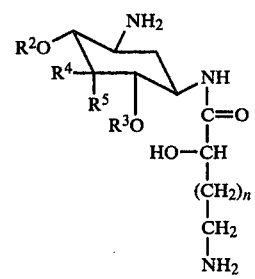

or a pharmaceutically acceptable acid addition salt thereof, wherein n is an integer of from 0 to 4; R$^2$ is a hexopyranosyl ring of the formula

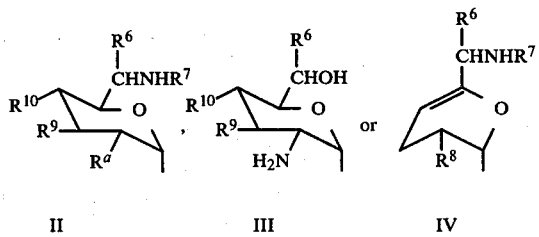

II    III    IV in which R$^6$ is H or CH$_3$, R$^7$ is H or CH$_3$, R$^8$ is OH or NH$_2$, R$^9$ is H or OH and R$^{10}$ is H or OH;

R$^3$ is H or a hexapyranosyl ring of the formula

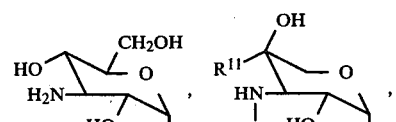

V    VI

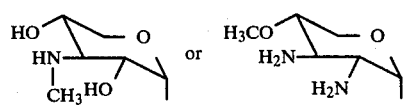

VII    VIII in which R$^{11}$ is H or CH$_3$;

R$^5$ is H or OH; and

R$^4$ is H, OH or a pentofuranosyl ring of the formula

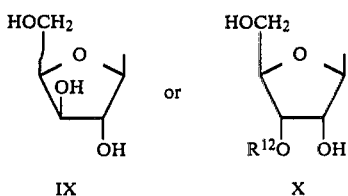

in which R$^{12}$ is H or a hexopyranosyl ring of the formula

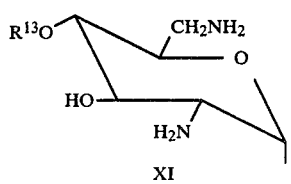

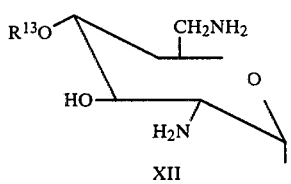

in which R$^{13}$ is H or α-D-mannopyranosyl;
provided that, when R$^3$ is other than H, one of R$^4$ and R$^5$ and H and the other is OH; and provided that, when R$^3$ is H, R$^5$ is H and R$^4$ is a pentofuranosyl ring of Formula IX or X;
which process comprises reacting a polysilylated aminoglycoside prepared from an aminoglycoside of Formula XIV

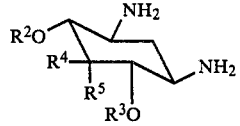

in which R$^2$, R$^3$, R$^4$ and R$^5$ are as defined above, and which contains from 0 to 3 conventional non-silyl amino-blocking groups on amino groups other than the C-1 amino group, in a substantially anhydrous organic solvent, with an acylating derivative of an acid of the formula

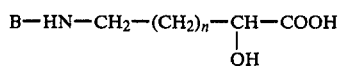

in which B is a conventional amino-blocking group and n is as defined above; and subsequently removing all blocking groups by conventional means.

2. A process for the preparation of a 1-N-[L-(−)-ω-amino-α-hydroxyalkanoyl]aminoglycoside of the formula

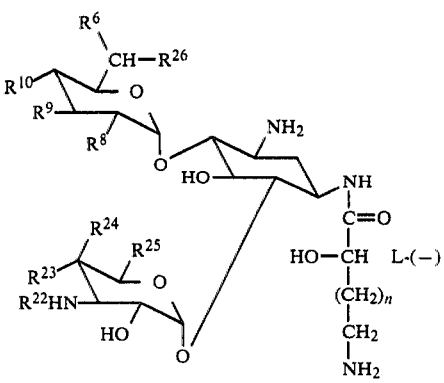

or a pharmaceutically acceptable salt thereof, wherein n is an integer of from 0 to 4, R$^6$ is H or CH$_3$, R$^8$ is OH or NH$_2$, R$^9$ is H or OH, R$^{10}$ is H or OH, R$^{22}$ is H or CH$_3$, R$^{23}$ is OH or CH$_3$, R$^{24}$ is H or OH, R$^{25}$ is H or CH$_2$OH, and R$^{26}$ is OH, NH$_2$ or NHCH$_3$; provided that, when R$^{22}$ is H, R$^{25}$ is CH$_2$OH, and when R$^{22}$ is CH$_3$, R$^{25}$ is H; and provided that, when R$^{23}$ is OH, R$^{24}$ is H, and when R$^{23}$ is CH$_3$, R$^{24}$ is OH;
which process comprises reacting a polysilylated aminoglycoside prepared from an aminoglycoside of the formula

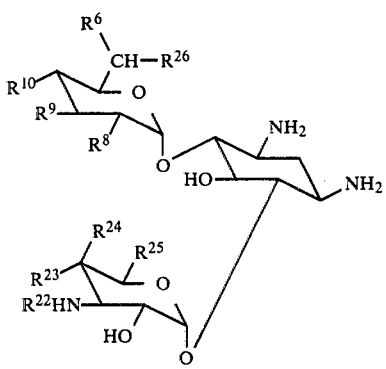

in which R$^6$, R$^8$, R$^9$, R$^{10}$, R$^{22}$, R$^{23}$, R$^{24}$, R$^{25}$ and R$^{26}$ are as defined above, and which contains from 0 to 3 conventional non-silyl amino-blocking groups on amino groups other than the C-1 amino group, in a substantially anhydrous organic solvent, with an acylating derivative of an acid of the formula

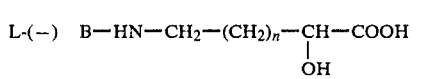

in which B is a conventional amino-blocking group and n is as defined above; and subsequently removing all blocking groups.

3. The process of claim 2 wherein the acylating derivative of the acid of Formula XIII is an active ester or a mixed acid anhydride.

4. The process of claim 3 wherein the amino-blocking group on the acylating derivative of the acid of Formula XIII is selected from those of the formulae

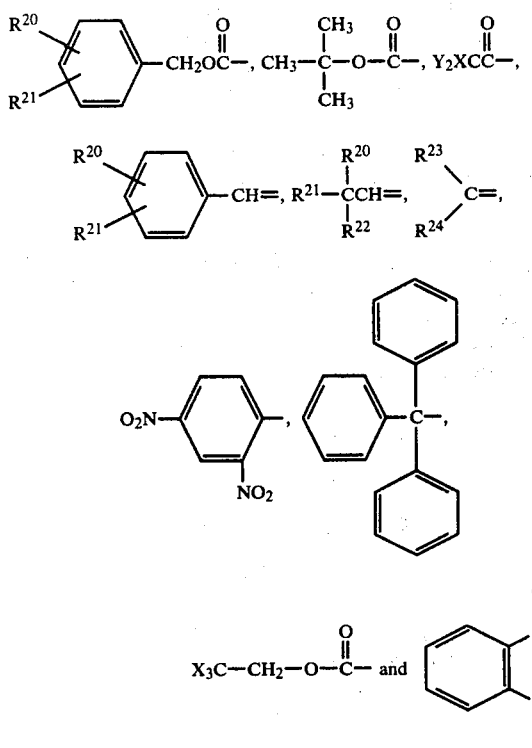

wherein $R^{20}$, $R^{21}$ and $R^{22}$ are alike or different and each is H, F, Cl, Br, $NO_2$, OH, (lower)alkyl or (lower)alkoxy, X is Cl, Br, F or I, Y is H, Cl, Br, F or I, $R^{23}$ is aryl or (lower)alkyl, each of which may be substituted by chloro, bromo, fluoro, nitro (lower)alkyl, or (lower)alkoxy, and $R^{24}$ is $-CH_2COOCH_3$, $-CH_2COOC_2H_5$ or $-CH_2COCH_3$; or $R^{23}$ and $R^{24}$, taken together with the carbon atom to which they are attached, represent a cyclopentylidene, cyclohexylidene or cycloheptylidene moiety.

5. The process of claim 4 wherein the acylating derivative of the acid of Formula XIII is its active ester with N-hydroxy-succinimide, N-hydroxy-5-norbornene-2,3-dicarboximide or N-hydroxyphthalimide.

6. The process of claim 4 wherein the acylating derivative of the acid of Formula XIII is its mixed anhydride with pivalic acid, benzoic acid, isobutylcarbonic acid or benzylcarbonic acid.

7. A process of claim 5 or 6 wherein the amino-blocking group on the acylating derivative of the acid of Formula XIII is carbobenzyloxy, trifluoroacetyl or t-butoxycarbonyl.

8. A process of claim 7 wherein the polysilylated aminoglycoside contains from 1 to 3 amino-blocking groups selected from carbobenzyloxy and trifluoroacetyl on amino groups other than the C-1 amino group.

9. A process of claim 7 wherein the polysilylated aminoglycoside is polysilylated gentamicin $B_1$ and n is 0.

10. A process of claim 9 wherein the polysilylated gentamicin $B_1$ contains an average number of trimethylsilyl groups per molecule of from 3 to 7.

11. A process of claim 8 wherein the polysilylated aminoglycoside is polysilylated 6'-N-methyl-3',4'-dideoxykanamycin B containing conventional non-silyl amino-blocking groups on the 2'- and 6'-amino moieties; and n is 0.

12. A process of claim 11 wherein the polysilylated 6'-N-methyl-3',4'-dideoxykanamycin B contains an average number of trimethylsilyl groups per molecule of from 3 to 5.

13. A process of claim 8 wherein the polysilylated aminoglycoside is polysilylated 4'-deoxykanamycin A containing conventional non-silyl amino-blocking groups on the 3- and 6'-amino moieties, and n is 0.

14. A process of claim 2, 3 or 4 wherein the polysilylated aminoglycoside is polysilylated 4'-deoxy-6'-N-methylkanamycin A containing conventional non-silyl amino-blocking groups on the 3- and 6'-amino moieties.

15. A process of claim 7 wherein the polysilylated aminoglycoside is polysilylated 4'-deoxy-6'-N-methylkanamycin A containing amino-blocking groups selected from carbobenzyloxy and benzyl on the 3- and 6'-amino moieties, n is 0, and the silyl groups are trimethylsilyl.

16. A process of claim 7 wherein the polysilylated aminoglycoside is polysilylated 4'-deoxy-6'-N-methylkanamycin A containing amino-blocking groups selected from carbobenzyloxy and benzyl on the 3- and 6'-amino moieties, n is 1, and the silyl groups are trimethylsilyl.

17. A process of claim 15 wherein the polysilylated 4'-deoxy-6'-N-methylkanamycin A contains an average number of trimethylsilyl groups per molecule of from 3 to 5.

18. A process of claim 16 wherein the polysilylated 4'-deoxy-6'-N-methylkanamycin A contains an average number of trimethylsilyl groups per molecule of from 3 to 5.

19. A polysilylated aminoglycoside prepared from an aminoglycoside of the formula

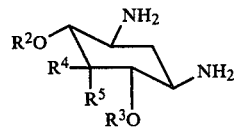

XIV wherein $R^2$ is a hexopyranosyl ring of the formula

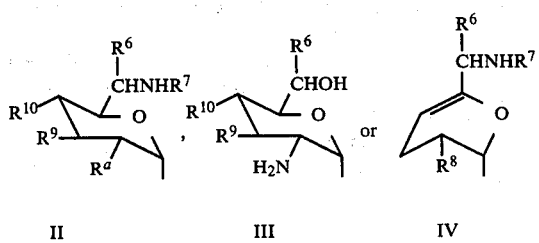

in which $R^6$ is H or $CH_3$, $R^7$ is H or $CH_3$, $R^8$ is OH or $NH_2$, $R^9$ is H or OH and $R^{10}$ is H or OH;

$R^3$ is H or a hexopyranosyl ring of the formula

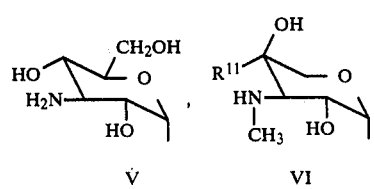

-continued

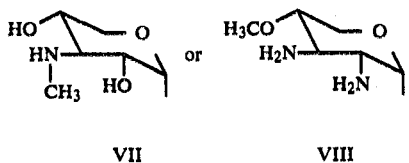

VII  or  VIII in which $R^{11}$ is H or $CH_3$;
  $R^5$ is H or OH; and
  $R^4$ is H, OH or a pentofuranosyl ring of the formula

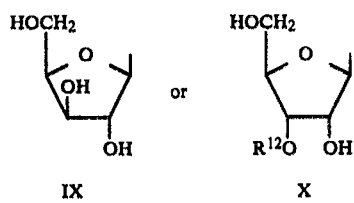

IX  or  X in which $R^{12}$ is H or a hexopyranosyl ring of the formula

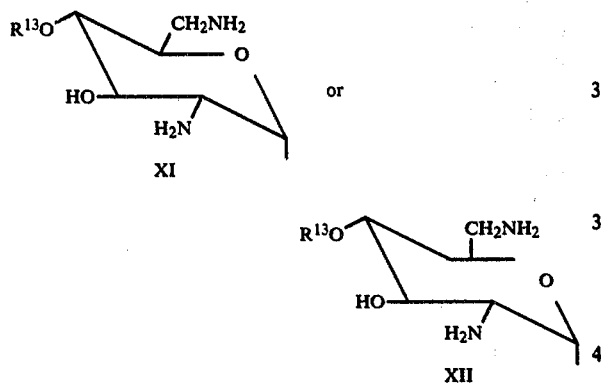

XI or

XII in which $R^{13}$ is H or α-D-mannopyranosyl;
  provided that, when $R^3$ is other than H, one of $R^4$ and $R^5$ is H and the other is OH; and provided that, when $R^3$ is H, $R^5$ is H and $R^4$ is a pentofuranosyl ring of Formula IX of X;
  said polysilylated aminoglycoside containing from 0 to 3 conventional non-silyl amino-blocking groups on amino groups other than the C-1 amino group.

20. A polysilylated aminoglycoside prepared from an aminoglycoside of the formula

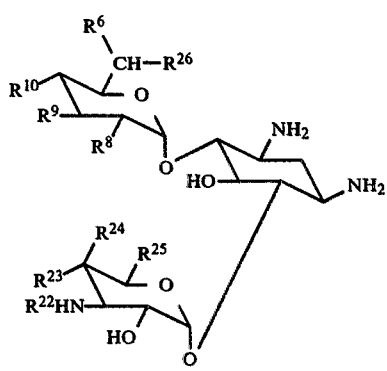

wherein $R^6$ is H or $CH_3$, $R^8$ is OH or $NH_2$, $R^9$ is H or OH, $R^{10}$ is H or OH, $R^{22}$ is H or $CH_3$, $R^{23}$ is OH or $CH_3$, $R^{24}$ is H or OH, $R^{25}$ is H or $CH_2OH$, and $R^{26}$ is OH, $NH_2$ or $NHCH_3$; provided that, when $R^{22}$ is H, $R^{25}$ is $CH_2OH$, and when $R^{22}$ is $CH_3$, $R^{25}$ is H; and provided that, when $R^{23}$ is OH, $R^{24}$ is H, and when $R^{23}$ is $CH_3$, $R^{24}$ is OH; said polysilylated aminoglycoside containing from 0 to 3 conventional non-silyl amino-blocking groups on amino groups other than the C-1 amino group.

21. A polysilylated aminoglycoside of claim 20 containing an average number of silyl groups per molecule of from 3 to 8.

22. A polysilylated aminoglycoside prepared from an aminoglycoside of the formula

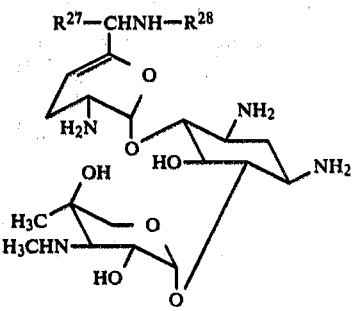

wherein $R^{27}$ is H or $CH_3$ and $R^{28}$ is H or $CH_3$; said polysilylated aminoglycoside containing from 0 to 3 amino-blocking groups other than silyl on amino groups other than the C-1 amino group.

23. A polysilylated aminoglycoside of claim 22 containing an average number of silyl groups per molecule of from 3 to 8.

24. A polysilylated aminoglycoside prepared from an aminoglycoside of the formula

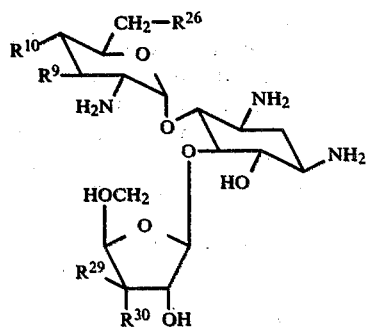

wherein
  $R^9$ is H or OH, $R^{10}$ is H or OH, $R^{26}$ is OH, $NH_2$ or $NHCH_3$,
  $R^{29}$ is H or OH, and $R^{30}$ is H, OH or $OR^{31}$, in which $R^{31}$ is a hexopyranosyl ring of the formula

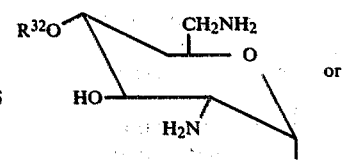

or

-continued

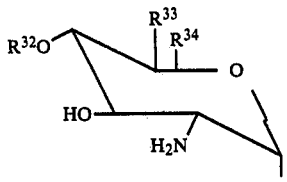

in which $R^{32}$ is H or α-D-mannopyranosyl, and one of $R^{33}$ and $R^{34}$ is H and the other is $CH_2NH_2$; provided that, when $R^{29}$ is H, $R^{30}$ is OH or $OR^{31}$, and that when $R^{29}$ is OH, $R^{30}$ is H; said polysilylated aminoglycoside containing from 0 to 3 conventional non-silyl amino-blocking groups on amino groups other than the C-1 amino group.

25. A polysilylated aminoglycoside of claim 24 containing an average number of silyl groups per molecule of from 3 to 8.

26. Polysilylated gentamicin $B_1$ containing from 0 to 3 conventional non-silyl amino-blocking groups on amino groups other than the C-1 amino group.

27. Polysilylated 6′-N-methyl-3′,4′-dideoxykanamycin B containing from 0 to 3 conventional non-silyl amino-blocking groups on amino groups other than the C-1 amino group.

28. Polysilylated 4′-deoxykanamycin A containing from 0 to 2 conventional non-silyl amino-blocking groups on amino groups other than the C-1 amino group.

29. Polysilylated 4′-deoxy-6′-N-methylkanamycin A containing from 0 to 2 conventional non-silyl amino-blocking groups on amino groups other than the C-1 amino group.

30. The polysilylated 4′-deoxy-6′-N-methylkanamycin A of claim 29 which contains amino-blocking groups on the 3- and 6′-amino moieties.

* * * * *

UNITED STATES PATENT AND TRADEMARK OFFICE
CERTIFICATE OF CORRECTION

PATENT NO. : 4,347,354

DATED : August 31, 1982

INVENTOR(S) : Martin J. Cron et al.

It is certified that error appears in the above—identified patent and that said Letters Patent is hereby corrected as shown below:

In Column 5, Line 60, structural formula II should read as follows:

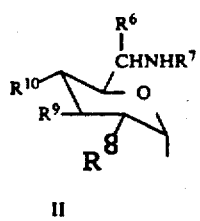

II

In Column 6, Line 43, structural formula XII should read as follows:

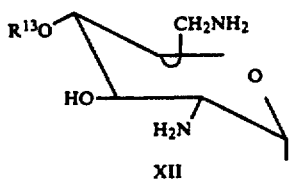

XII

In Column 38, Line 35, structural formula II should read as follows:

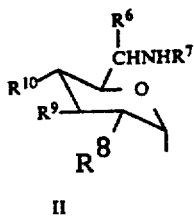

II

UNITED STATES PATENT AND TRADEMARK OFFICE
CERTIFICATE OF CORRECTION

PATENT NO. : 4,347,354
DATED : August 31, 1982
INVENTOR(S) : Martin J. Cron et al.

It is certified that error appears in the above—identified patent and that said Letters Patent is hereby corrected as shown below:

In Column 39, Line 25, structural formula XII should read as follows:

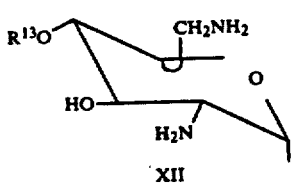

In Column 39, at Line 34, the first occurrence of the word "and" should read -- is -- .

In Column 42, Line 50, structural formula II should read as follows:

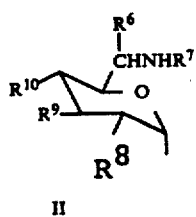

In Column 43, Line 37, Formula XII should read as follows:

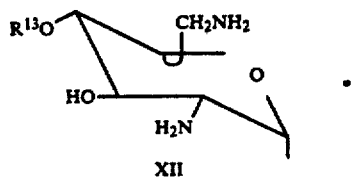

UNITED STATES PATENT AND TRADEMARK OFFICE
CERTIFICATE OF CORRECTION

PATENT NO. : 4,347,354

DATED : August 31, 1982

INVENTOR(S) : Martin J. Cron et al.

It is certified that error appears in the above—identified patent and that said Letters Patent is hereby corrected as shown below:

In Column 43, Line 47, the phrase "Formula IX of X" should read -- Formula IX or X -- .

In Column 44, the structural formula at Line 64 (last structure in that column) should read as follows:

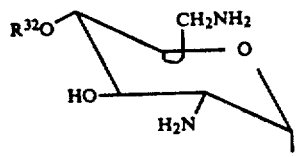

The structural formula at the top of Column 45 should read as follows:

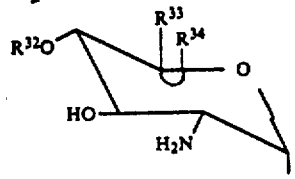

Signed and Sealed this

Twenty-third Day of November 1982

[SEAL]

Attest:

Attesting Officer

GERALD J. MOSSINGHOFF

Commissioner of Patents and Trademarks